United States Patent [19]

Donehoo, III

[11] Patent Number: 5,007,431
[45] Date of Patent: Apr. 16, 1991

[54] APPARATUS AND METHOD FOR UPDATED RECORDING OF IRREGULARITIES IN AN ELECTROCARDIOGRAM WAVEFORM

[75] Inventor: Robert F. Donehoo, III, Huntsville, Ala.

[73] Assignee: Care Systems, Inc., Huntsville, Ala.

[21] Appl. No.: 189,833

[22] Filed: May 3, 1988

[51] Int. Cl.$^5$ .............................................. A61B 5/04
[52] U.S. Cl. .................................. 128/696; 364/413.06
[58] Field of Search ............... 128/696, 702, 703, 704, 128/706, 710; 364/413.05, 413.06

[56] References Cited

U.S. PATENT DOCUMENTS

| | | | |
|---|---|---|---|
| 4,475,558 | 10/1984 | Brock .................................. | 128/710 |
| 4,628,327 | 12/1986 | Anderson et al. ................... | 128/710 |
| 4,665,485 | 5/1987 | Lundy et al. ........................ | 128/710 |
| 4,742,458 | 5/1988 | Nathans et al. ................. | 364/413.06 |

Primary Examiner—Francis Jaworski
Assistant Examiner—George Manuel
Attorney, Agent, or Firm—Phillips & Beumer

[57] ABSTRACT

A system for detecting, recording, and maintaining, on an updated priority basis, segments of electrocardiogram (ECG) waveforms containing unusual activities, and including the characteristics of the event including the segment of ECG waveform containing the event, the type of event, the age (A) of the event, the weighting factor (WF) of the event, and the total number (T) of such events stored at an occurrence of the arrival of a new event, and comprising a first storage device (FIG. 1) for temporarily storing the characteristics of each newly arrived event and the individual Ts for each type of event, N memory blocks (MBs) (FIG. 3) for storing, on a basis updated with the arrival of each new event, the characteristics of N events, each stored in a separate MB. Also provided is a first logic (FIG. 4) for determining the highest product of A×WF×T, which identifies the MB containing the lowest priority event (LPE), herein known as the LPEMB, a second logic (FIG. 6) responsive to the identification of the MB containing the LPEMB (FIG. 4) to decrement by 1 the value of T contained in each MB contained in the LPEMB and in the first storage device, and a third logic (FIGS. 7 and 8) responsive to the decrementing of T by the second logic to enter the characteristics of the newly arrived event in the LPEMB, replacing the old event stored therein, and to increment by a value of T in each MB, other than the LPEMB, containing the same type of event as the new type of event entered into the LPEMB.

20 Claims, 11 Drawing Sheets

APPARATUS AND METHOD FOR UPDATED RECORDING OF IRREGULARITIES IN AN ELECTROCARDIOGRAM WAVEFORM

FIELD OF THE INVENTION

This invention relates generally to a method and an apparatus for recording and maintaining, and for constantly updating on a priority basis, types of electrocardiograph (ECG) waveforms containing unusual activities, herein referred to as events. More specifically, this invention relates to such an apparatus wherein certain characteristics of the ECG waveform including a section of the ECG waveform, the type of event, the number of such type of events, the age of event, and a weighting factor reflecting the importance of the event are stored in a memory and replacing an event with the lowest priority with a new event, with the event being replaced being determined by a consideration of its age, weighting factor, and number of such type of events then stored in the memory.

GENERAL BACKGROUND OF THE INVENTION

Prior art cardiac monitors often contain a feature which stores short segments of a patient's waveform for events detected by the prior art system. These events, commonly called a recall event, may be viewed at a later point in time which may be more convenient, or a history of the patient's events may be viewed in a single session. One problem frequently exhibited in traditional arrhythmia recall strategies is in the procedure for replacing recall events already stored by the system by new, more recent events. Often, the system will require the user to peruse the recall events or manually edit out the undesired events. Another prior art approach is to always place the new event in the place where the oldest event is kept, i.e., has been kept.

The most important characteristics associated with recalling events are typically:
  the type of event;
  the number of events of that type;
  the age of the event.

No known system employs the aforementioned three typical important characteristics to compute, on a priority basis, that event which has the lowest priority and which would be replaced by a new event. It would mark a definite improvement in the art to provide a recall system which employs the aforementioned three important characteristics in order to maintain a constantly updated record of the events which would be able to provide a better representation of a patient's arrhythmic activity. The present invention provides such a system.

OBJECTS AND FEATURES OF THE INVENTION

A primary object of the invention is to calculate the priority of the stored events at the end of every small predetermined interval of time by an algorithm involving the weighting factor of each event, the total number of each type of stored event, and the age of each event, and then replacing the event calculated to have the lowest priority with a new event just received, the new event being contained in a small section of the ECG waveform of the patient.

A second object is to update the total of each type of event and the age of each type of event each time a new event replaces a previously stored event since the number of previously stored events of the given type of which one is being replaced is reduced by one so that the total of that type event is reduced by one and the total type of the new event being entered is increased by one. Further, the age of all events except the new one being entered into the storage means must be incremented by an interval of time equal to the elapsed time since the last updating of age occurred.

A feature of the invention is to provide a logic arrangement responsive to a patient's ECG waveform to detect the type of events occurring in each equal and contiguous time segment of such ECG waveforms and to assign a weighting factor in accordance with the type event determined. A bank of N memory blocks for storing the characteristics of each ECG waveform segment and including the weighting factor, the total of each type event and the age of each event with one event being stored in each memory block, and connecting logic including timing means for gating the waveform segment, the weighting factor, the total of the particular type of event event analyzed into the correct memory block which will overwrite and thereby erase the previously determined stored event having the lowest priority of stored events.

In accordance with another feature of the invention, the priority of each event is determined by the product of the weighting factor, the total of that type event stored in the bank of memory blocks, and the age of such event.

In accordance with still another feature of the invention, each memory block has a permanent address and logic responsive to such permanent address and the product of the weighting factor, the total of each type of event, and the age of each event to produce an output address pointing to that memory block which contains the event with the lowest priority which is to be replaced by the incoming new event.

In accordance with yet another feature of the invention, there is provided logic which responds to the conditions when the system is first energized and the memory bank is completely empty to enter each incoming event consecutively into the memory block having the lowest address and the next event into the memory block having the next lowest address, and so on until all N memory blocks are filled, at which time a newly arrived event must replace an event already stored, and the prior system described briefly above is then activated.

BRIEF SUMMARY OF THE INVENTION

In a preferred form of the invention, there is provided a system for detecting, recording, and maintaining, on an updated priority basis, segments of electrocardiogram (ECG) waveforms containing unusual cardiac activities and including the characteristics of the event, such as the segment of ECG waveform containing the event, the type event, the age (A) of the event, the weighting factor (WF) of the event, add the total number of such events (T) stored at an occurrence of the arrival of a new event, and comprising a storage device for temporarily storing the characteristics of each newly arrived event and the T for each type of event, N memory blocks (MBs) for storing, on a basis updated with the arrival of each new event, the characteristics of N events, each stored in a separate memory block, first logic including an algorithm employing A, WF, and T of the event contained in each memory block for identifying the memory block containing the lowest priority event (LPE), herein known as the LPEMB, second logic responsive to the identification of the memory block containing the LPEMB and in said storage device, and third logic responsive to the decrementing of T by the second logic to enter the characteristics of the newly arrived event in the LEPMB, replacing the old event stored therein and to increment by the value of T in each memory block, other than the LPEMB, containing the same type event as the new type event entered into the LPEMB.

GENERAL DISCUSSION OF SYSTEM ORGANIZATION AND OPERATION THEREOF

Because of the relative complexity of this invention, it is divided into sections in accordance with the following outline defining the subject matter of the area of the invention discussed in that section.

Figure 1:
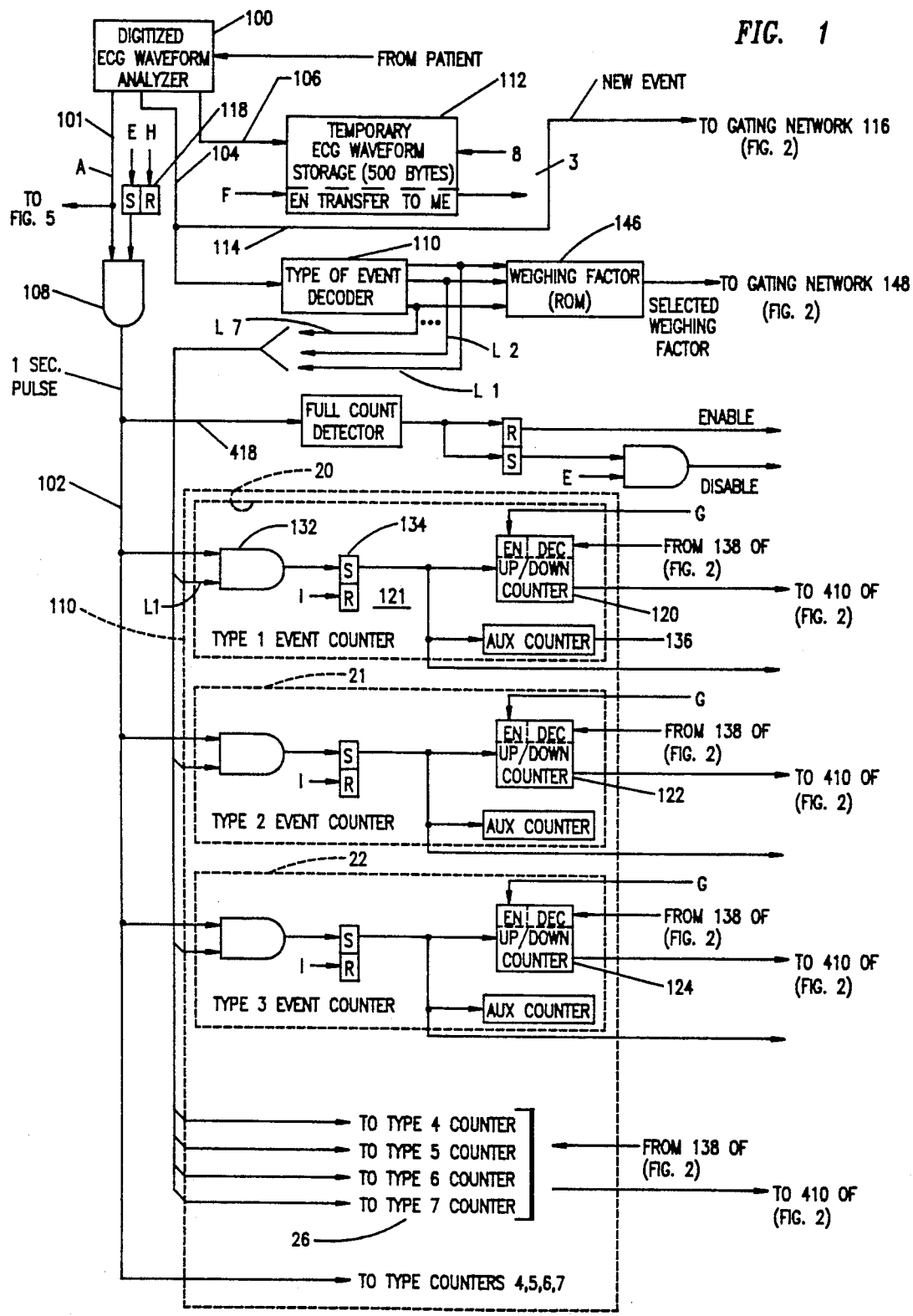
FIG. 1 shows logic for detecting, receiving, and temporarily storing the characteristics of a newly arrived event.
Figure 2:
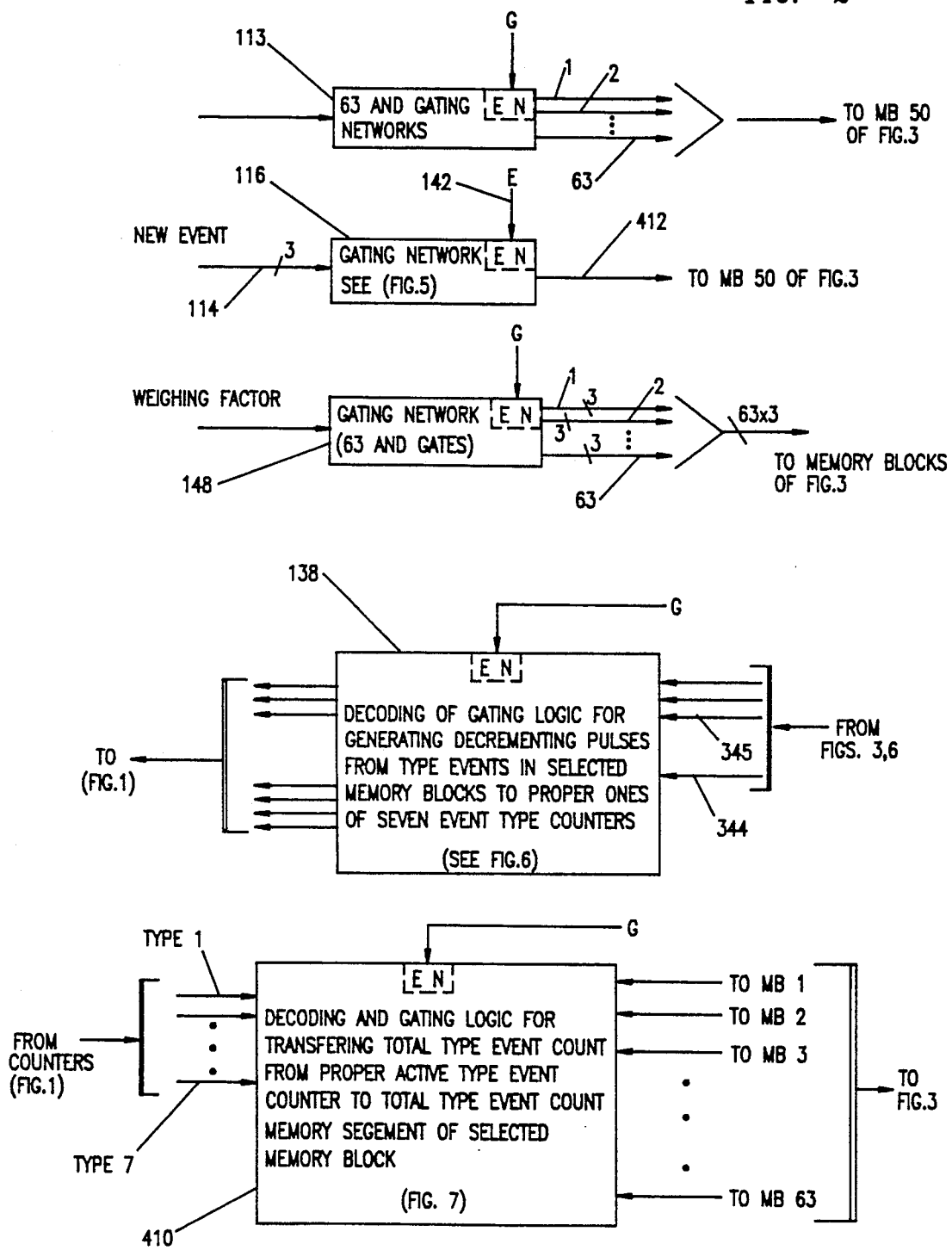
FIG. 2 shows gating networks enabling information to pass back and forth between the logic of FIGS. 1 and 3 to perform the required updating as new events are received.
Figure 3:
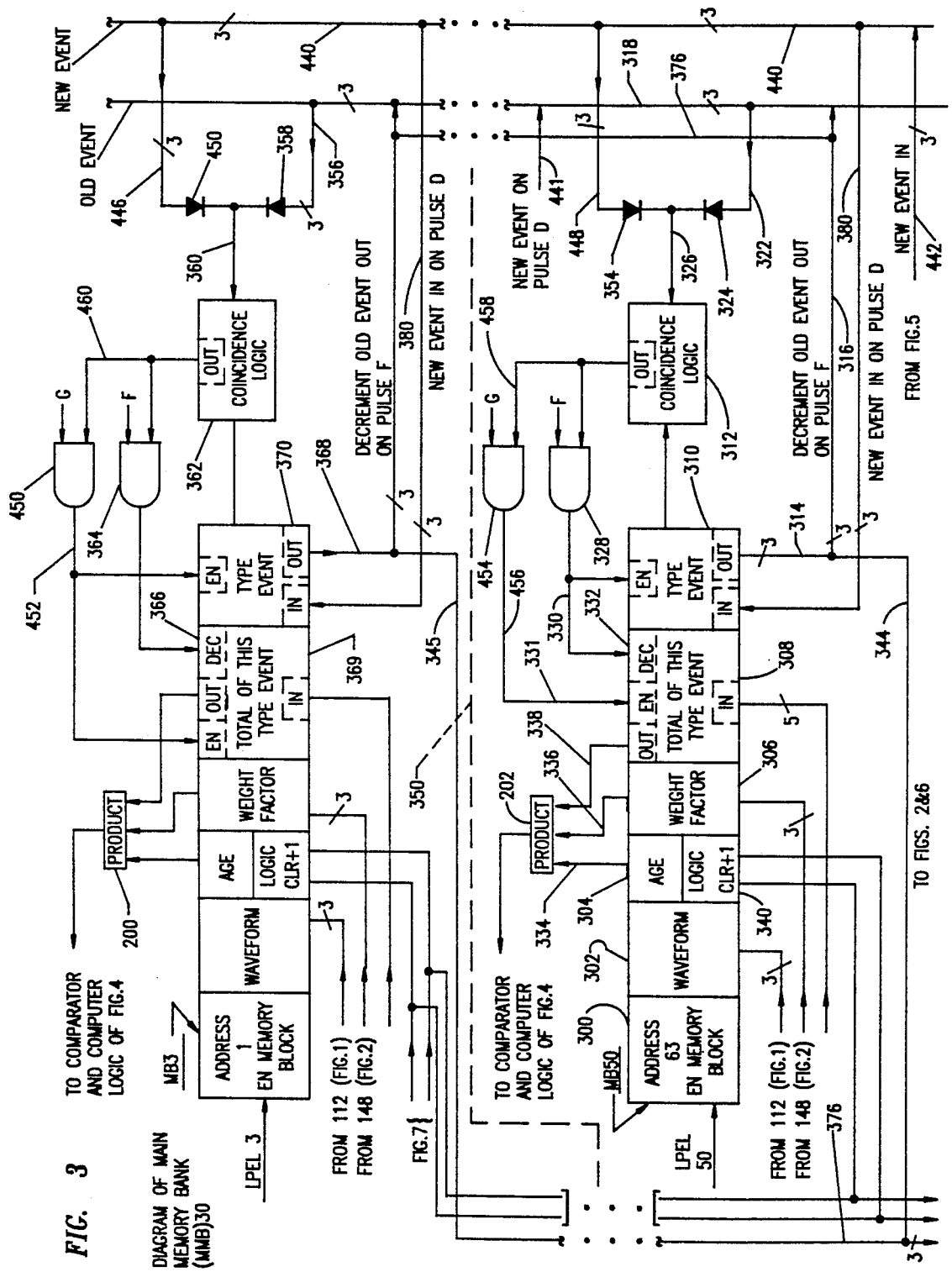
FIG. 3 shows memory and logic for the storing of a plurality of events with logic for constantly updating such storage as new events arrive.
Figure 4:
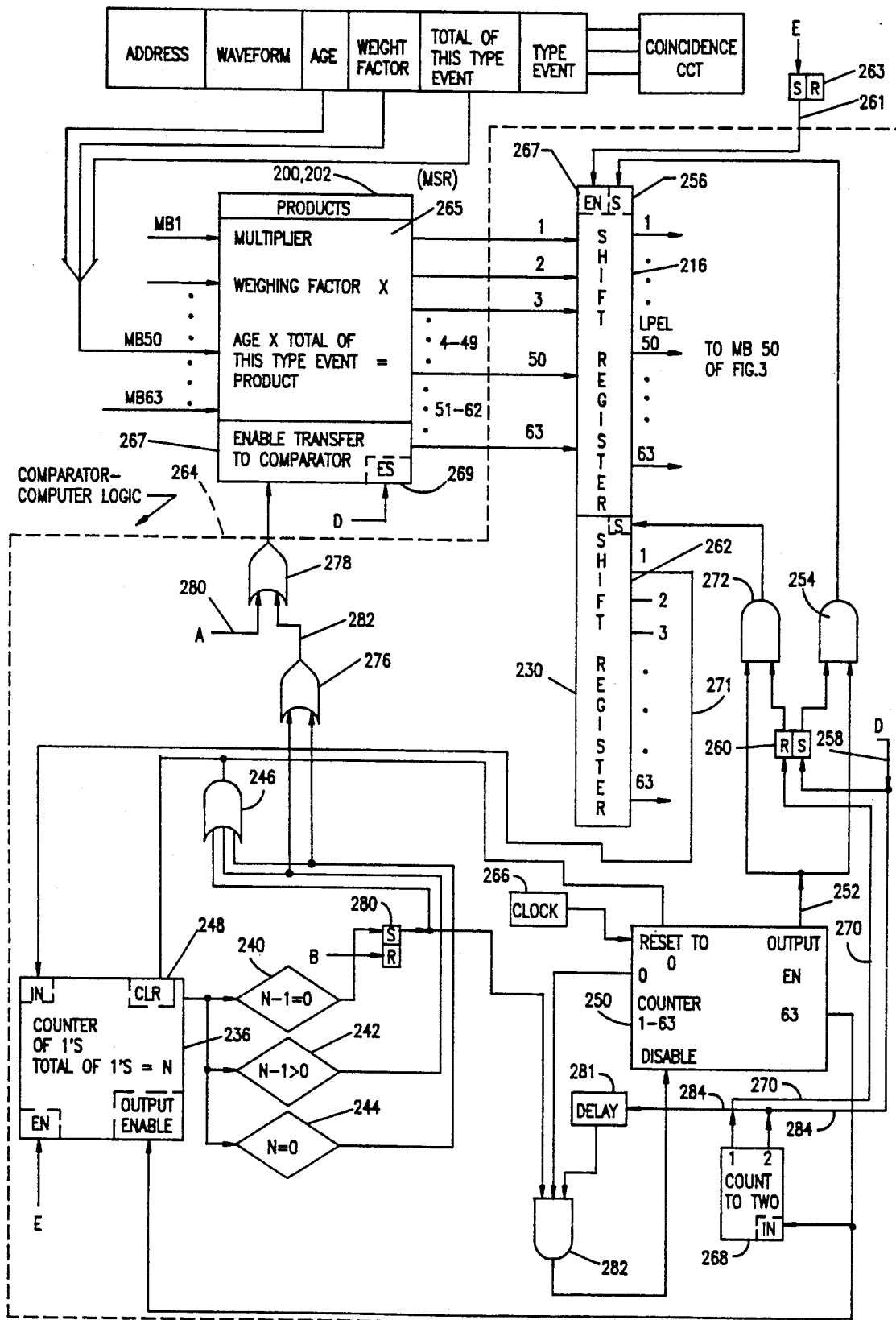
FIG. 4 shows logic for determining which event stored in the memory of FIG. 3 has the lowest priority and should be replaced by the newly arrived event.
Figure 5:
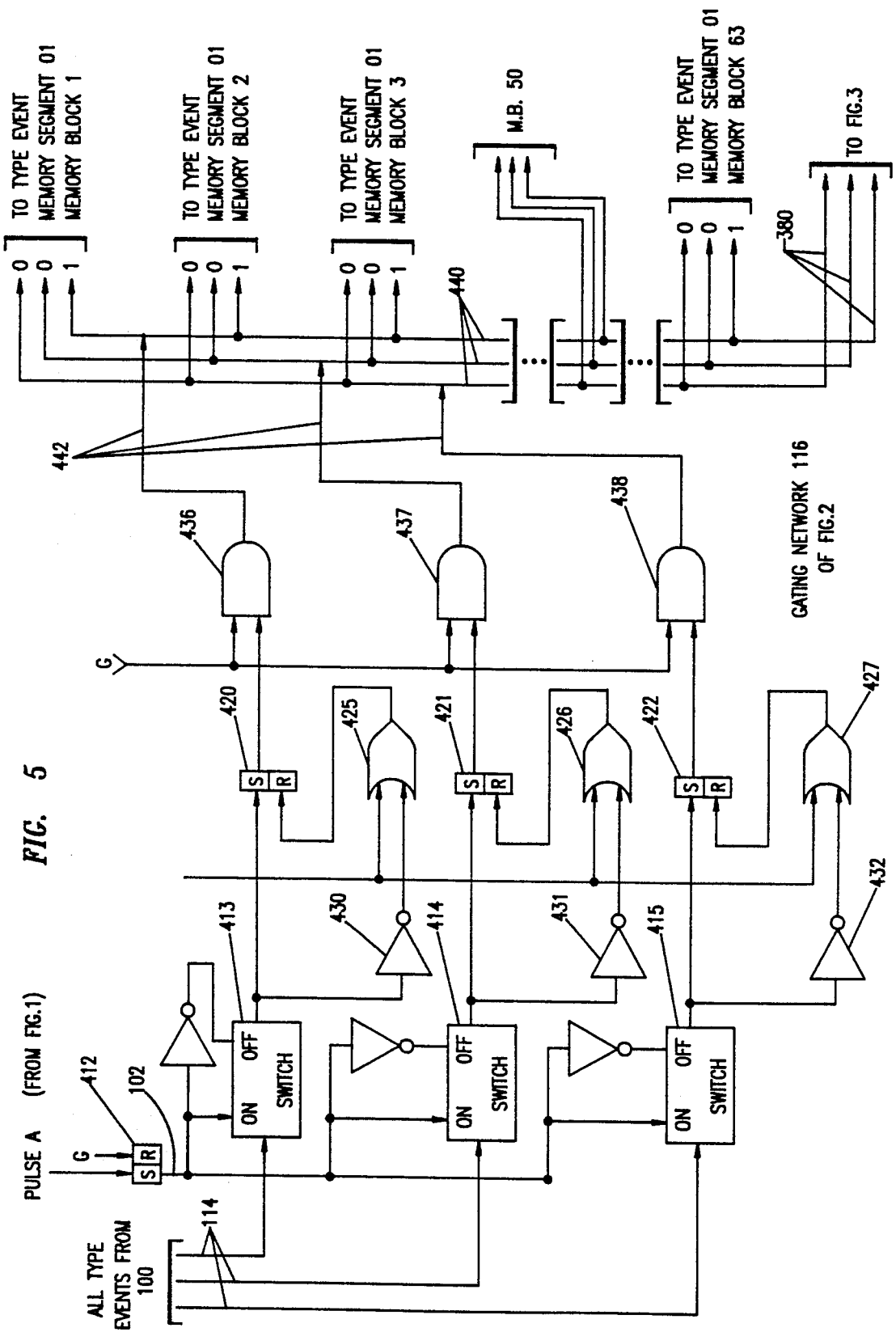
FIGS. 5-8 show detailed logic diagrams of the general gating logic diagrams of FIG. 2.
Figure 6:
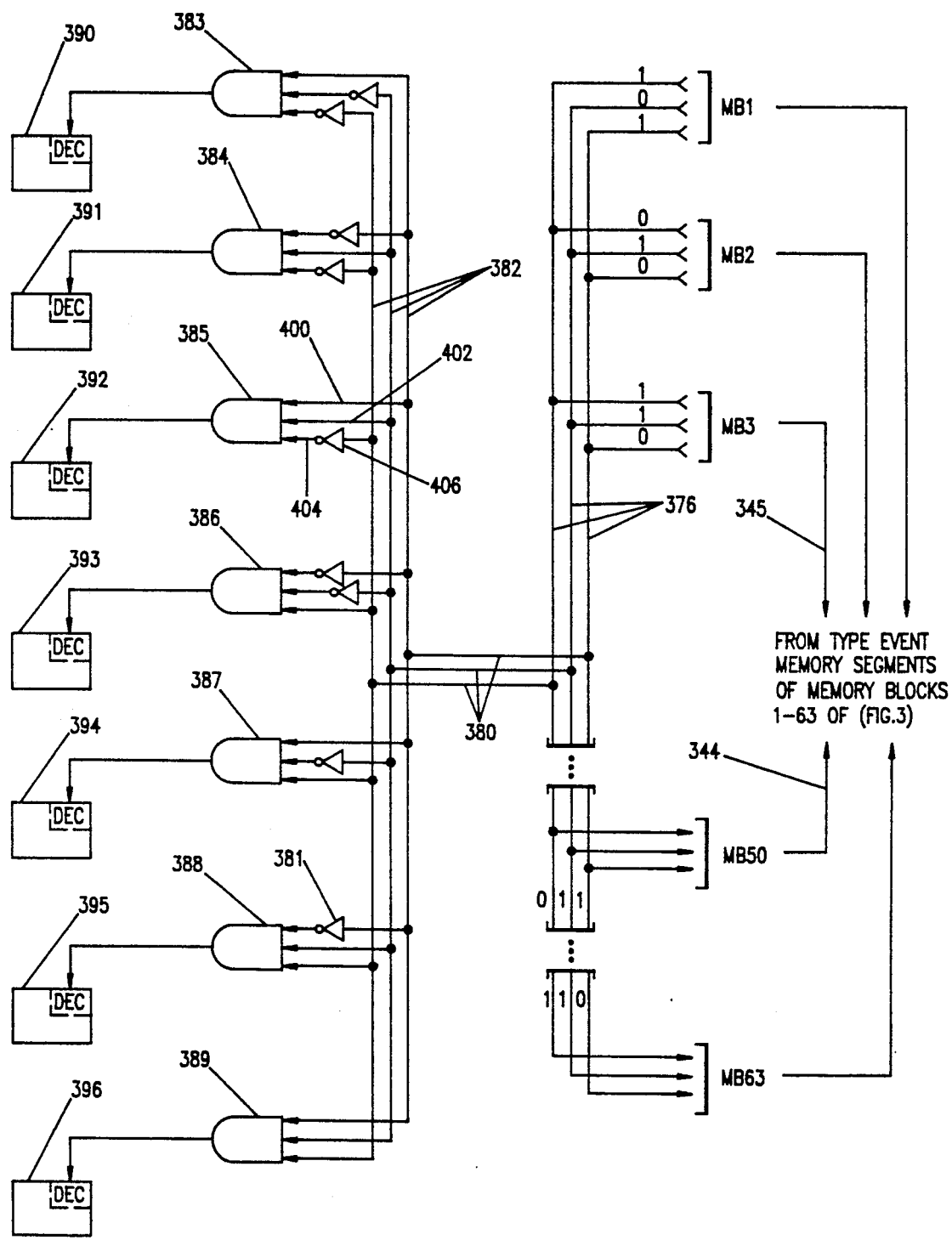
Figure 7:
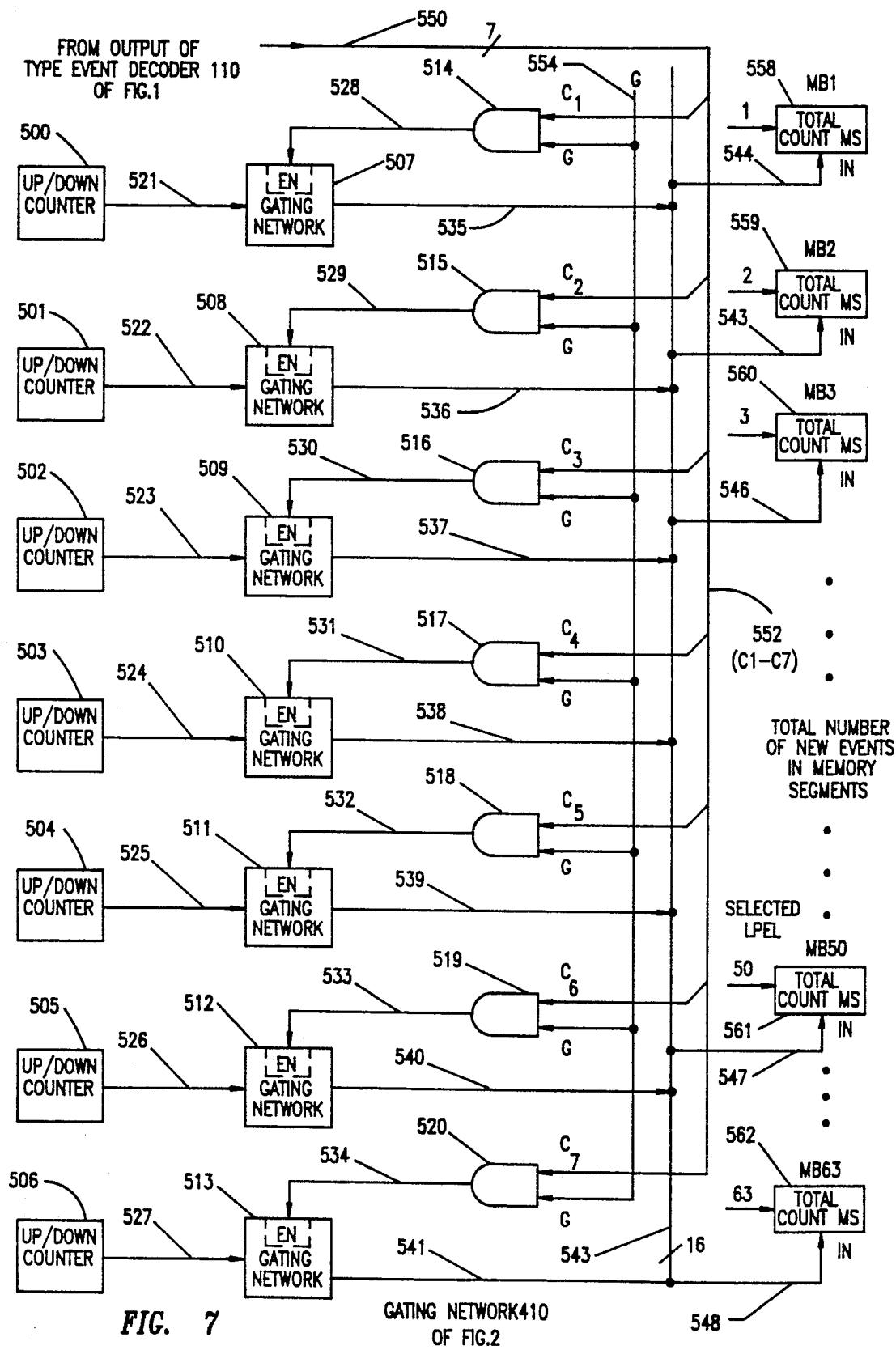
Figure 8:
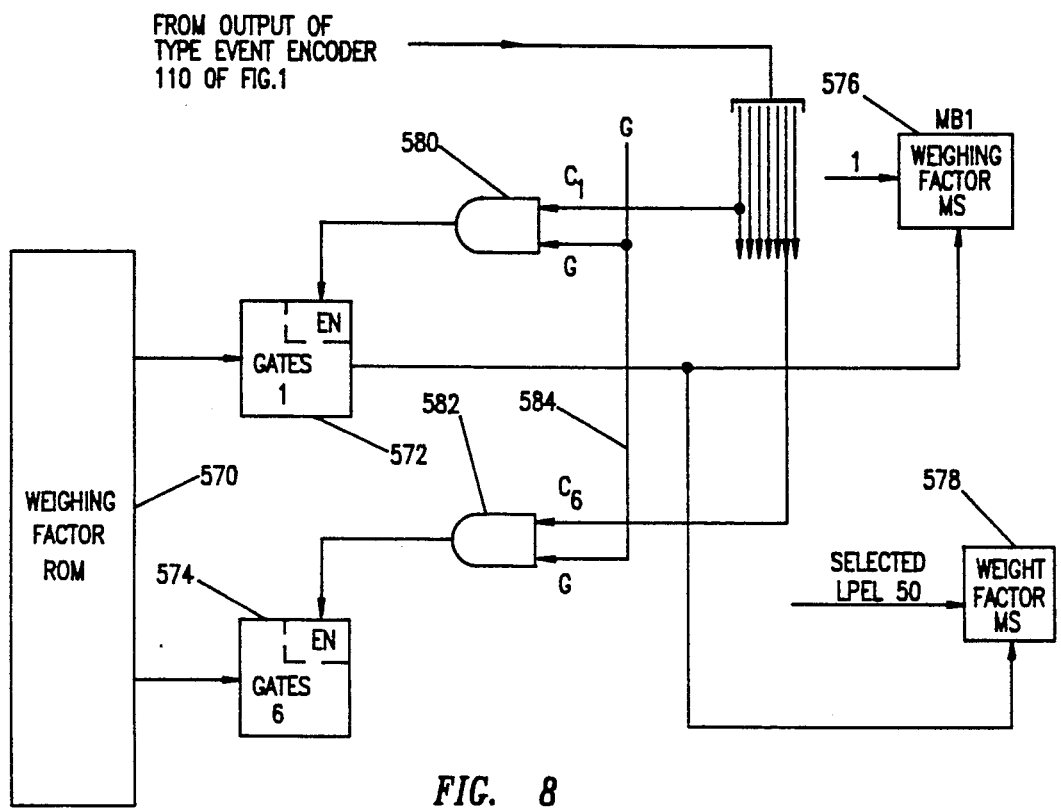
Figure 9:
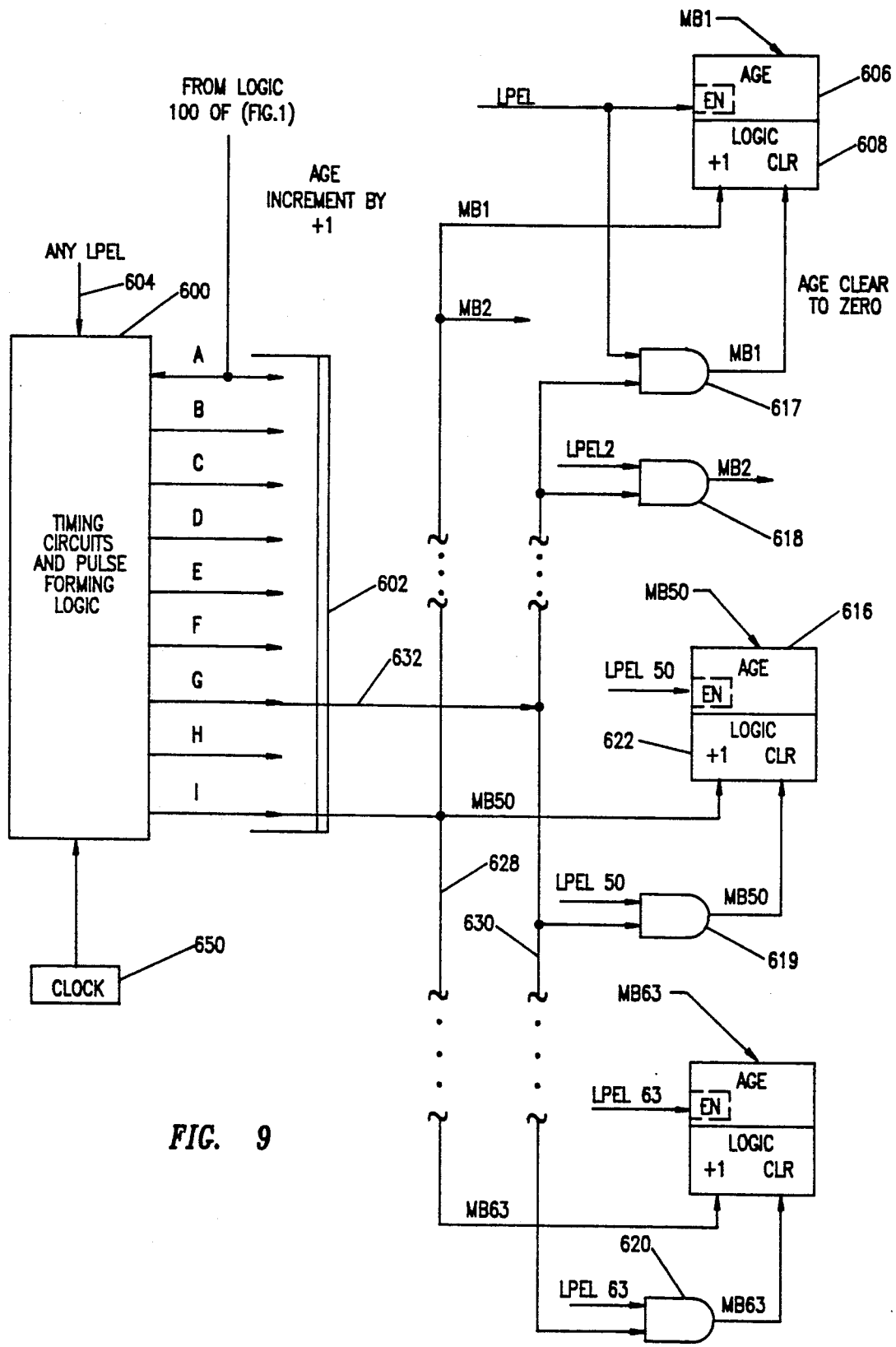
FIG. 9 shows timing logic for generating the timing pulses required by the system.
Figure 10:
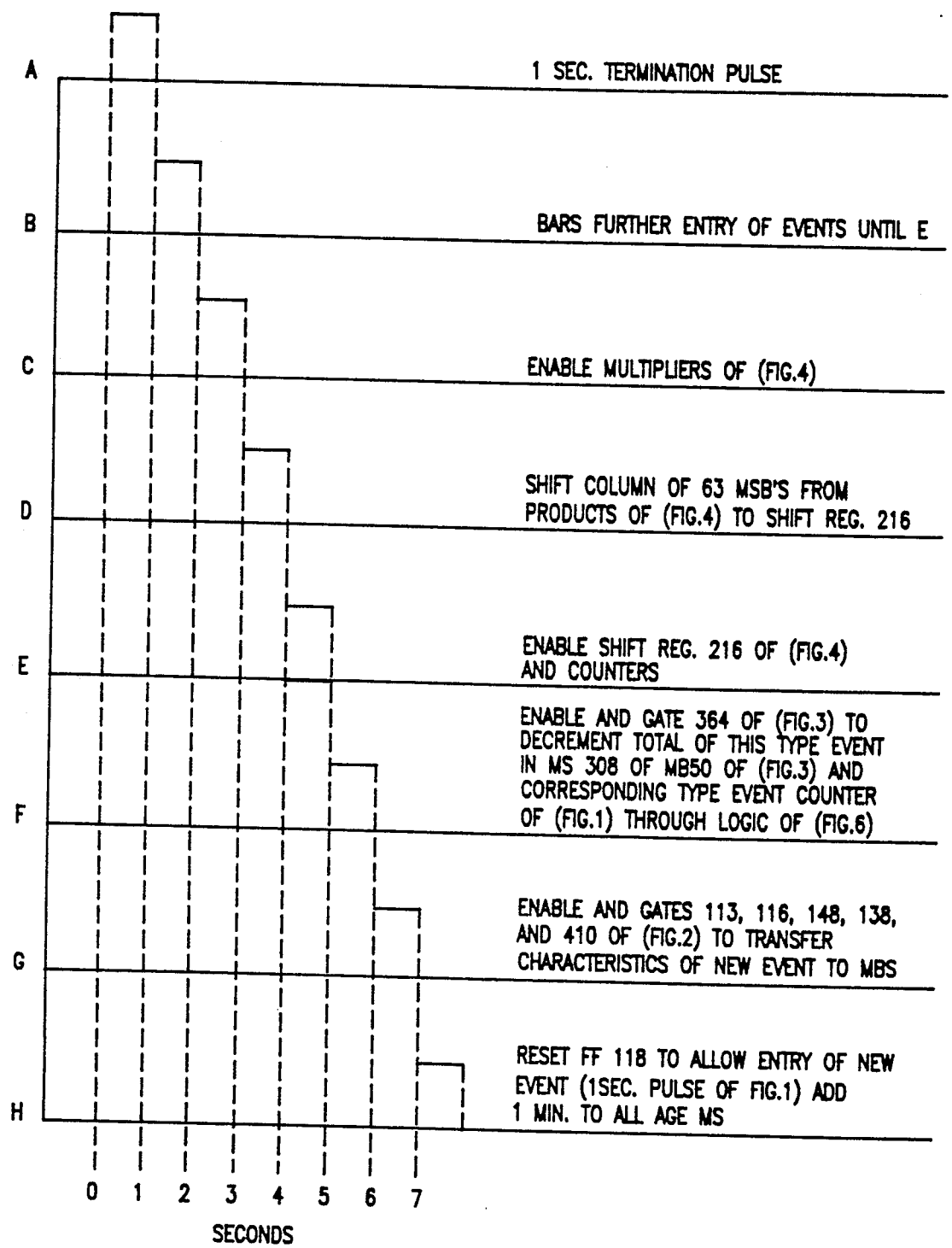
FIG. 10 is a timing chart showing the timing pulses generated by the timing logic of FIG. 9.
Figure 11:
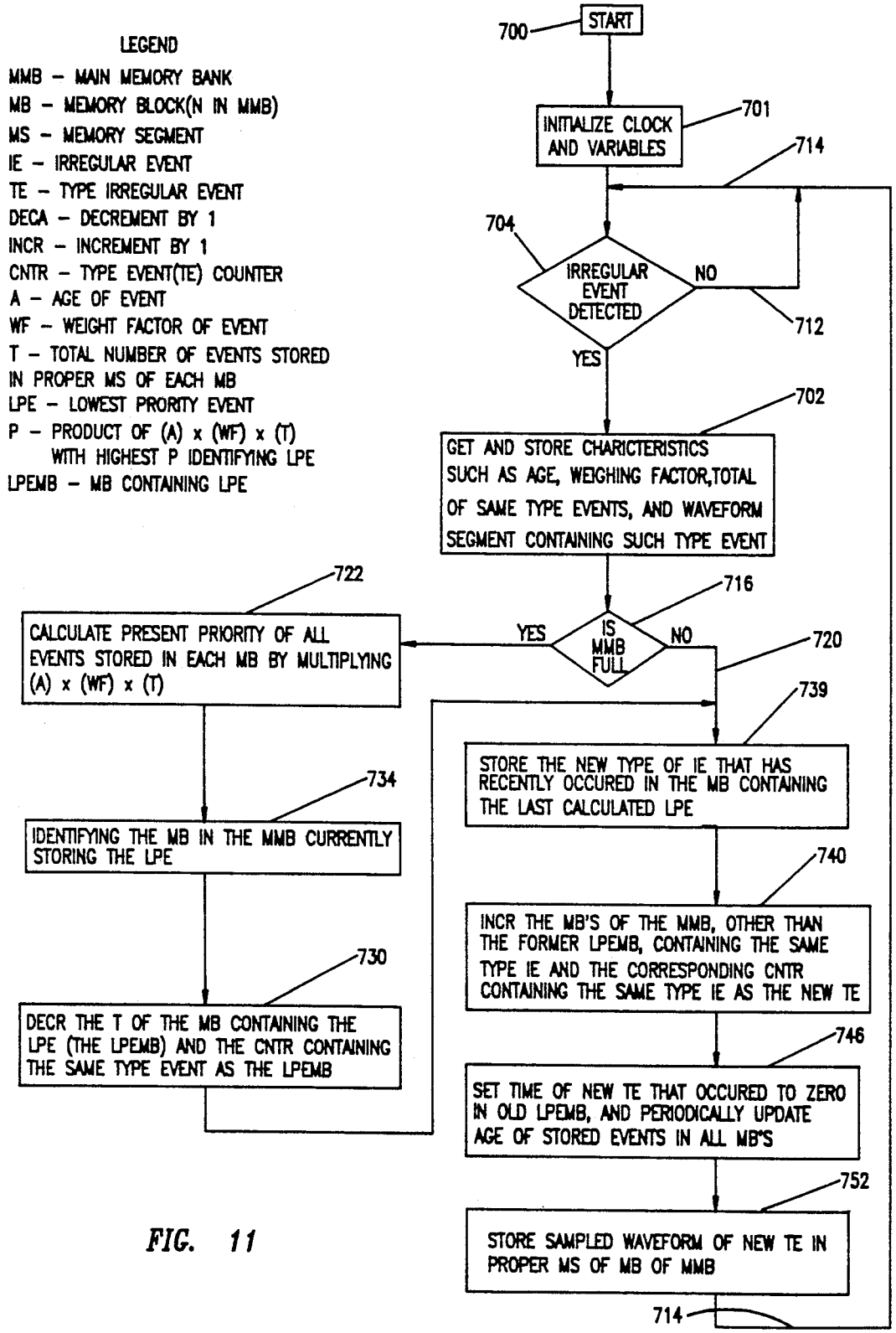
FIG. 11 is a diagram of a logic flow chart of the method of the invention.

General Background of the Invention
Objects and Features of the Invention
Brief Summary of the Invention
Brief Description of the Drawings
General Discussion of System Organization and Operation Thereof
Detailed Discussion of the Invention
Storage Characteristics of a Newly Arrived Event Including New Total Count, Weighting Factor, Type Event, and Entry of that Portion of the Four Second ECG Waveform into Temporary Storage (FIGS. 1-3 and 10)
Discussion of Logic for Memory Block Containing Lowest Priority Event (FIG. 4)
Decrementing of Event Counters of FIG. 1 and Entering the New Event into the Proper Memory Blocks of FIG. 3
Discussion of FIG. 6
Entry of New Event Characteristics into the Memory Blocks of FIG. 3
Discussion of FIG. 5
Discussion of FIG. 7
Discussion of FIG. 8
Discussion of FIGS. 9 and 10
Discussion of flow chart of FIG. 11

Before discussing each of the 11 figures of the invention in detail, an overall description of the invention will be set forth in order to facilitate a basic understanding of the relationship between the logic of the 11 figures of the drawings and the timing relationship between the functions of such 11 figures.

The sequence of events that must occur in the logic are not straightforward in the sense that one conclusion must be reached employing a first section of the logic before a second conclusion can be reached affecting a second portion of the logic, and then the results of the second conclusion can be employed in furthering the first conclusion in order to arrive at a third conclusion employing another portion of the logic. The foregoing is set forth generally below in the step sequence of the logical events that must occur in the system in order to continuously update the record of events and their characteristics as each new event occurs.

As discussed above, an event is an irregular pattern or event occurring in the ECG waveform which is considered abnormal. There are several types of such irregular events which are listed below preceeding the listing of the sequence of recording and updating such events in a suitable memory bank so that an observer can instantaneously recall upon a screen the current record of the characteristics of such events, including the waveform pattern of the most recent event, the age of the event measured from the time the event was first entered into the memory system, a weighting factor dependent upon the importance of the event, the total number of the type event stored in the N (for example, N can equal 63) memory blocks constituting the entire memory bank, and the type event stored in any particular memory block. The memory bank is comprised of a plurality of 63 memory blocks, each of which in turn contains a number of memory segments each containing one of the characteristics of the event as described above.

Following is a listing of eight types of events with definitions of each type event. However, only the first seven type events are recognized by the present invention. The eighth type event is not.

Following the definition of the eight types of events is a listing of the weighting (retention) factors thereof with examples explaining the significance of such weighting factors.

Generally, all other factors being equal, the higher the weighting factor, the sooner such event will be replaced in the main memory of FIG. 3 since it is the event whose product of age, total type of such events in the entire memory bank, and weighting factor is the event that has the lowest priority and is replaced first.

ARRHYTHMIA ANALYSIS EXAMPLE DEFINITIONS

NOTE: These are only example definitions. The clinical interpretation of the heart's electrical activity represented by an ECG waveform is an art practiced by physicians often requiring case history studies to accurately define some of the types of arrhythmia detections described.

1. LONG RR—If the distance between two detected heart beats is greater than the user specified limit, then this is considered a missed beat which, in our systems, is called a long RR due to the lengthened R to R interval duration.

2. NON-CAP—If the patient has a pacemaker and there is an R to R interval of greater than or equal to two times the normal R to R interval, then this is considered as a pacemaker noncapture event.

3PVC—If a heart beat occurs which is premature, widened, and results in a compensatory pulse following it before the next heart beat, then our system identifies this as a premature ventricular contraction (PVC). There are many variances on the theme of the characteristics required for this type of event. The foregoing is simply a specific example.

4. COUPLET—If two PVCs occur consecutively, then the pair of PVCs is identified as a Couplet as well as having been counted as two PVC events (stored in recall only once).

5. SALVO—If three or more PVCs occur consecutively, then they are given the identity as a Salvo as well as having been counted as three PVC events (stored in recall only once).

6. TACH—If the heart rate rhythm changes from some normal value to a fast rhythm for at least four heart beats and the heart beats do not result in wide ECG waveform complexes (i.e., indicative of ventricular activity), then this will be given the identity of a tachycardia (TACH).

7. VTACH—If the heart rate rhythm changes from some normal value to a fast rhythm for at least four heart beats and the heart beats result in wide ECG waveform complexes (i.e., indicative of ventricular activity), then this will be given the identity of a ventricular tachycardia (VTACH).

8. VFIB—If the ECG waveform is composed of rapid, repetitive series of chaotic waves each differing from the other with a repetitive rate of between two and seven per second, then this will be given the identify of ventricular fibrillation (VFIB).

| WEIGHTING FACTOR EXAMPLES | |
|---|---|
| LONG RR | 10 |
| NON-CAPTURE | 7 |
| PVC | 50 |
| COUPLET | 5 |
| SALVO | 3 |
| TACH | 2 |
| VTACH | 1 |

The above weighting factors define the ratio of the amount of time a particular event type is kept in the main memory bank (MMB) relative to the other types of events.

EXAMPLES

1. VTACH events are maintained 50 times longer than a PVC and 10 times longer than a LONG R—R, etc.

2. COUPLET events are maintained 10 times longer than a PVC and 2 times longer than a LONG R—R, etc.

ABBREVIATIONS USED IN SPECIFICATION AND CLAIMS

Because certain terms are used to frequently herein, abbreviations have been adopted therefor and are often used in lieu of the full spelling, as follows:
MS—Memory Segment
MB—Memory Block
MMB—Main Memory Bank
LPE—Lowest Priority Event
LPEL—Lowest Priority Event Lead
LPEMB—Memory Block Containing Lowest Priority Event
MSR—Multiplier Storage Register (265-FIG. 4)
CCL—Comparator-Computer Logic (264-(FIG. 4)
MSB—Most Significant Bit
DL—Decision Logic

LISTING OF SEQUENCE OF STEPS OF SYSTEM OPERATION

1. Any new event occurring in the patient's ECG waveform must first be identified as to the type event it is and then entered into one of several event type counters of FIG. 1 (seven in the design of this invention), each of which is unique to that particular type of event. A full second must expire after the recognition of the new event before such new event can be entered into the proper type event counter. However, it is to be noted that the new event is not entered into the MMB (FIG. 3) at this time for reasons which will be discussed later.

2. The entry of the new event into the appropriate type event counter triggers an energizing pulse which energizes a multiplication process (FIG. 4), which in turn determines the lowest priority event (LPE) stored in the MMB and the address thereof. The multiplication consists of multiplying the age of the event by the weight factor of the event and then by the total of this type of event stored in all of the 63 MBs of the MMB.

3. If it is assumed that there are 63 MBs, then there will be 63 such products which will be compared in suitable comparator logic. The event having the lowest priority will be replaced by the new event just arriving. The event having the lowest priority (LPE) in the 63 memory blocks will appear in one of 63 outputs of the comparator as the highest product for reasons to be discussed briefly above and to be discussed in detail later herein.

4. The output lead of the 63 output leads of the comparator indicating the MB containing the LPE will be hereinafter referred to as the lowest priority event lead (LPEL), and such signal will be used in a number of places in the circuit to activate other parts of the logic, as will be discussed later.

5. The LPEL will be supplied directly to the selected MB containing the LPE to energize all of the memory segments (MSs) in said MB so that the contents of each MS can be processed in its proper time sequence as other parts of the system logic are energized by other energizing timing signals, as shown in FIG. 10, and which will be discussed as such timing signals occur in the discussion of the operation of the system.

6. Energization of the proper LPEL will cause the type event stored in the proper MS of the corresponding MB to be supplied to a common three-lead cable which is connected to the type event MSs of all of the memory segments of all of the 63 MBs of the bank of memory.

7. A coincident circuit associated with each MB will then compare the type of event supplied to the common cable with the type of event stored in each of the 63 MBs, and, if coincidence occurs, the total of this old type of event will be decremented by one in all of the MBs containing this type of event but not including that MB in which a new event will later be entered, as will be discussed later. The MB in which the new event is to be entered will have the new total of the new type of event entered into the appropriate MS of the LPEL of the MB selected by the comparator.

8. Next, the logic of FIGS. 1, 2, and 9, are activated by appropriate timing signals of FIG. 10 to store the ECG waveform, the total number of new types of events in the particular type of event counter which received a new event, the weighting factor of the new event, and the updated age, which will be zero, since the new event has just arrived in only that MB which contained the old type of event containing the LPE and which is now being replaced by the new event and its character.

9. The coincidence circuits mentioned above in step 7 are employed in entering the new total of the new event into all of the memory blocks previously containing the new type of event plus the memory block from which the old event is being removed, since the new event is supplied to a common lead, which in turn is supplied to all of the 63 memory blocks through the aforementioned coincidence circuit.

10. The system is now ready for the acceptance of a new event which will follow the sequence of the nine steps set forth above.

It should be noted that timing pulses (FIG. 10) are generated which store continuous and contiguous four-second segments of the incoming ECG waveform in a temporary storage 112 of FIG. 1, and that any events occurring more than one second plus the additional short timing pulses of FIG. 10 required to perform the logic steps enumerated above will be recorded in the memory banks even though they occur within the same four-second time period. After the termination of the four seconds, the ECG waveform stored in the temporary storage 112 will be transferred to the proper memory segment in the appropriate memory block of the memory bank of FIG. 3 identified by the LPEL, and a new four-second storage segment of the incoming ECG waveform will begin accumulating in the temporary storage 112.

It should further be noted that the incoming ECG waveform enters the temporary four-second storage means 112 of FIG. 1 continuously and passes through such four-second storage register continuously so that the four-second storage register is essentially a sliding window of the incoming ECG waveform and every four seconds will take a snapshot, so to speak, of the existing ECG waveform occuring during the four-second period beginning with the next newly arrived event, within that four-second period and will record events in the main memory bank if they meet the time distances described briefly above between new arriving events.

DETAILED DISCUSSION OF THE INVENTION

Storage Characteristics of a Newly Arrived Type of Event Including New Total Count, Weighting Factor, Type of Event, and Entry of that Portion of the Four-Second ECG Waveform into Temporary Storage (FIGS. 1-3 and 10)

Referring now to FIG. 1, the digitized ECG waveform analyzer, herein referred to as the ECG wavform analyzer 100, outputs three signals on output leads 102, 104, and 106, respectively, to AND gate 108 through flip-flop (FF) 118, type event decoder 110, and temporary ECG waveform storage 112, respectively.

More specifically, the type of newly received event, which can be any one of seven selected events, detectable by waveform analyzer 100, is supplied not only to the type of event decoder 110 through lead 104 but also to a gating network 116 of FIG. 2, to be described later herein in FIG. 8 in more detail.

Consider now logic element 100 which is a prior art device manufactured by Care Systems, Inc., 2005 Bob Wallace Avenue, Huntsville, Ala., and on sale and available to members of the public upon request. Logic element 100 is identified as MS 5005 Central Station Cardiac Monitoring System of Model Series 5000—Patient Monitoring Systems and functions to monitor the ECG waveform of a heart patient and to identify irregular events and the types thereof as they occur. A continuous ECG waveform is also generated both as visible recording and as a series of binary bytes which measure the amplitude of the ECG waveform and which can be recorded as an analog or a binary coded output.

Logic element 100 is also capable of detecting the occurrence of an irregular event and initiating a timing pulse which will mark a time interval of, for example, one second after the detection of the irregular event. If another irregular event of more importance should occur before the end of the one-second period, the first event is ignored in the system but is, of course, recorded.

Literature describing the MS 5005 Central Station Monitoring System is also available from Care upon request.

Figure 1A:
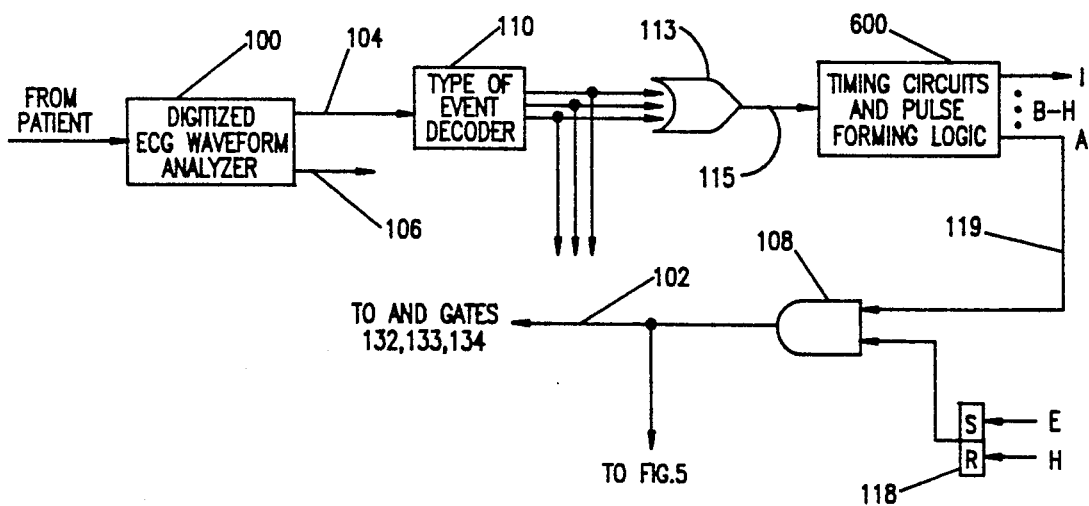
FIG. 1a shows logic related to timing of the system.

The signal applied to lead 101 from waveform analyzer 100 of FIG. 1 is a one-second pulse which is employed to measure the minimum time that the new event must exist after detection by waveform analyzer 100 in order to be defined as a valid event. If a second, more important, event, with the importance being determined by a weighting factor selected by weighting factor logic 146, occurs before the expiration of the aforementioned one second, then the first newly arrived event type is ignored and the second, more important, event is the event type that is recognized by the system and the characteristics thereof stored in the various storage elements of FIG. 1 and ultimately in the MMB of FIG. 3, as will be discussed in detail later. In FIG. 1, it is assumed that the one-second pulse is generated within waveform analyzer 100. Alternately, one-second pulse A of FIG. 10 can be generated by the logic external of analyzer 100 of FIG. 1a in the following manner.

When an event is decoded by type of event decoder 110 (FIG. 1), there will be at least a binary 1 included in the three-lead coded output which will be supplied through OR gate 113 to input 115 (FIG. 1a) of timing circuits and pulse forming logic 600 of FIG. 9 which will, after one second, supply pulse A from timing logic 600. Pulse A is supplied via lead 119 to one input of AND gate 108 of FIG. 1. The other input to AND gate 108 is also supplied with a binary 1 since FF 118 is normally set. Thus, AND gate 108 supplies a one-second pulse A to one-second pulse lead 102 which performs the same functions as the one-second pulse alternately on lead 101, and fed to AND gate 108, of FIG. 1. The occurrence of pulse A in FIG. 9 initiates the occurrence of the following pulses B-I.

The logic to determine whether a second event occurring before the expiration of the one-second pulse is more important than the preceding event is determined by the normally set FF 118 of FIG. 1 which, when set by pulse E of FIG. 10, will enable AND gate 108. FF 118 is reset by timing pulse H of FIG. 10 to disable AND gate 118 immediately after expiration of the one-second pulse, thereby preventing other types of new events from entering a type of event counter of FIG. 1.

If a second event occurs after the one-second pulse plus the short timing pulses of FIG. 10 have occurred, then such second event, as mentioned above, will be recognized by the system and the characteristics thereof recorded in the temporary storage elements of FIG. 1 and ultimately in the MMB of FIG. 3.

The one-second pulse, designated as pulse A in the timing chart of FIG. 10, passes through enabled AND gate 108 and to the seven up-down type of counters within the dotted block 110 of FIG. 1. Three of these up-down counters, 120, 122, and 124, and their associated logic are contained in the smaller dashed line blocks 20, 21, and 22 of FIG. 1, which are included within the larger, previously mentioned dashed line block 110. Also, symbolically represented at the bottom of the structure within the dashed line block 110 are the four remaining up-down type of event counters and their associated logic, each identified by one of the phrases "to type four-seven counter," for example.

As discussed above, briefly, it is necessary to identify the old type event stored in the main memory bank of FIG. 3 which contains the lowest priority event (LPE) and then to identify all other MBs in the MMB containing the same type event in order to decrement the total number of such old type of events in each MB containing such old type of events before the new event can be entered into that particular MB which has been determined to contain the LPE.

Thus, that particular up-down counter of counters 120, 122, or 124, or the other four up-down counters which record a particular one of the seven types of events, and which has been incremented by the newly arrived event, must store that event until the decrementing of the old type of event in the MMB of FIG. 3 has been accomplished.

Assume, for example, that the new type of event is a type #1 event. Such type #1 event will be decoded by decoder 110 which has seven output leads, labeled 1-7, with lead #1 being connected to one input of AND gate 132 of the up-down type of event counter 120 of logic 121. At the occurrence of the one-second pulse A on lead 102, AND gate 132 will become enabled to set flip-flop 134, thereby incrementing the count in up-down counter 120 by one. It should be noted that auxiliary counter 136 is also incremented by one, but auxiliary counter 136 is not an up-down counter so that the count within auxiliary counter 136 can never be decremented but will always contain the actual total number of type #1 events received by the system, whereas up-down counter 120 can be decremented and consequently can have a count contained therein different from that of auxiliary counter 136.

As will be seen later from a discussion of FIGS. 2 and 7, the total count accumulated in any of the up-down counters within block 110 of FIG. 1 cannot pass through the decoding and gating circuit 410 of FIG. 2 until timing pulse G of the timing waveforms of FIG. 10 occurs. The timing pulses of FIG. 10, except for the one-second pulse A, are generated by the timing circuit and pulse forming logic 600 of FIG. 9.

Timing pulse E will not occur until the decrementing of the total count of the old event in those memory blocks of the main memory bank which contained the type of old event to be eliminated from the memory block containing the LPE of the memory bank has occurred. Such decrementing of the total number of old events in the main memory bank is effective upon the occurrence of timing pulse E of the timing pulses of FIG. 10.

Similarly, the newly received type of event appearing on lead 114 of FIG. 1 is not supplied to the type of event memory segment 310 of the memory block 50 of FIG. 3 until pulse E is supplied to lead 142 of FIG. 2, which enables the gating network 116 to permit the new event to pass therethrough the then to all of the type of event MSs of all of the MBs of the MMB, such as the type of event memory segment 310. However, it is to be noted that by means of the coincidence circuits in FIG. 3, such as coincidence circuit 312 (MB 50), which exist in all of the 63 memory blocks and some associated logic, only those memory blocks containing the old event type which is present in the memory block containing the LPE will be decremented. Such decrementing logic will be discussed in more detail layer.

Referring again to FIG. 1, the output of the type of event decoder 110 is supplied to weighting factor ROM 146 which selects one of seven weighting factors. It is to be noted that the output of type of event decoder 110 consists of seven leads, each corresponding to an individual one of seven weighting factors stored in ROM 146. The output of ROM 146 is supplied to gating network 148 (FIG. 2) which has 63 sets of three outputs each. Each of the 63 sets of three outputs go to an individual one of the weighting factor memory segments of one of the 63 memory blocks of FIG. 3. Thus, the weighting factor appearing on output lead 1 of gating network 148 will be supplied to the weighting factor memory segment 306 of memory block 50 of the memory bank of FIG. 3. However, such weighting factor will not be entered into memory segment 306 of FIG. 3 until the occurrence of timing pulse G, which enables gating network 148.

It should be noted that the new event output of gating network 116 and the weighting factor output of gating network 148 are supplied only to memory block 50 since memory block 50 has been identified as containing the lowest priority event (LPE). As discussed above, such LPE containing memory block is determined by the multiplication of the age, the weighting factor, and the total of this type (the old type) of event which is effected by the multiplication and comparator-computer logic of FIG. 4, as will be discussed in detail later in FIG. 4.

The transfer of the ECG waveform from temporary storage 112 (FIG. 1) into the proper one of the waveform memory segments of the 63 memory blocks does not necessarily occur at the same time as the storage of the new event, the weighting factors, or the new total count of the type of event.

The four-second period of ECG waveform appearing in the temporary waveform storage 112 is also stored in the waveform storage memory segment 302 of the appropriate MB containing the LPE which is now removed from that MB. In the example being described, the MB is MB 50, and a new four-second waveform segment will be stored in MS 302 of such MB 50 in FIGS. 3.

Discussion of Logic for Memory Block Containing Lowest Priority Event (FIG. 4)

However, before any of these characteristics of the new event can be stored in MB 50 of FIG. 3 containing the LPE, such LPE must first be determined. As mentioned above, such determination is made by the logic of FIG. 4 which is, in fact, the first logical operation to be performed after the temporary storage of the various characteristics of the new event in the various temporary storage elements of FIG. 1, as described above.

Such determination of the memory block determining the LPE must be made even before the total of the old type of event in the memory block containing the LPE can be decremented. Accordingly, a discussion of the means by which the determination of which memory block contains the lowest priority event will first be made in the following paragraphs with the aid of the logic diagram in FIG. 4, followed by a return to a discussion of FIG. 3 to more fully discuss recognition of those memory blocks containing an event having the LPE followed by the decrementing of the total of this type of event in all of the memory blocks containing such LPE type of event.

It perhaps should be noted at this time that the single memory block containing the LPE will not only ultimately have the new type of event entered therein but will also have the new total (T) of such new type of event entered in the MS containing the total of such new type of memory segment.

Before leaving the logic diagram of the memory block of FIG. 3, it is to be noted that each of the 63 memory blocks of the memory banks, of which only two are shown in FIG. 3, have a product logic identified by reference characters 200 and 202, respectively. These product logic blocks function to multiply the age times the weight factor times the total of the type of event in all of the memory blocks containing such a type of event and then supplying such product to the logic of FIG. 4, to which the discussion will now turn.

In FIG. 4, it will be assumed that the memory block containing the LPE is memory block 50, which is shown at the top of FIG. 4 and is a repetition of memory block 50 shown in FIG. 3 except for some omitted auxiliary logic. Product logic 200 of FIGS. 3 and 4 consists of a multiplier 265 (FIG. 4) which produces a binary number containing the product of the three characteristics of the event described above.

The binary product of multiplier 265 is stored in a plurality of 63 shift registers which are capable of shifting out their contents one bit at a time in parallel with each other, beginning with the most significant bit (MSB). These MSBs are shifted out simultaneously to shift register 216 of FIG. 4 which is part of a comparator-computer combination logic (FIG. 4) for determining which of the memory blocks contains the lowest priority event. Such shifting of succeeding MSBs from the product storage registers of multiplier 265 to shift register 216 is done in parallel upon a pulse supplied to an enable shift input 269 of storage registers 267 which occurs at the completion of all the multiplication required in the 63 memory blocks and is accomplished by means of timing pulse D.

Once shift register 216 contains the MSBs of the 63 products stored in the 63 registers of product logic 202, a pulse is supplied to enable input 267 of shift register 216 via lead 261 from the set output of FF 263 to cause the contents of shift register 216 to shift downwardly into shift register 230, with each bit in turn passing the first bit positions 262 of shift register 230. If such passing bit position contains a binary one, this one is applied to one's counter 236 via lead 271 to cause counter 236 to count from 0 to 1.

When the next MSB passes by the first bit position 262 of shift register 230 as the contents of shift register 216 are shifted downwardly, if such next MSB is a one, then counter 236 will count from 1 to 2 and contain a resultant count of 2.

In a similar manner, the remaining 61 bits contained in shift register 216 will be shifted, one by one, most significant bits first, from shift register 216 to shift register 230, and, as each bit passes the #1 bit position 262 of shift register 230, counter 236 of FIG. 4 will note whether such bit position contains a 1 or a 0, and if it contains a 1, counter 236 will add 1 count to its contents. If such bit position contains a 0, then counter 236 will not increase its count. At the end of comparison of the 63 bits contained in shift register 216 with the #1 bit position 262 of shift register 230, counter 236 is cleared to 0 in preparation for the comparison of the next 63 MSBs transferred from storage of multiplier 265 to shift register 216.

It should be noted that up to this point, the discussion of FIG. 4 has been a general description of multiplier-storage register (MSR) 265 and the general operation of shift registers 216 and 230 as well as counter 236. It should be noted that the logic in the lower half of FIG. 4, including the AND gates, the OR gates, the flip-flops, and decision logics 240, 242, and 244, all constitute a part of comparator-computer logic (CCL) 264 and functions to determine when a shift will occur from shift register (SR) 216 to SR 230 as well as when the next most significant bits of the 63 products stored in product storage register 202 will be shifted from MSR 265 to shift register 216 in parallel. Such logic in the lower half of FIG. 4 will be described in more detail later. For the present, the reader's attention is again directed to the general function of logic 265 and shift registers 216 and 230.

Once the 63 bits of a particular MSB of the 63 products stored in storage register 265 has been shifted into shift register 216 and then subsequently shifted downwardly in a series manner into shift register 230, with all of the binary 1's being counted in counter 236, the contents of shift register 230 will then always be shifted back up into shift register 216 for reasons to be described below.

Each time the shifting of the 63 bits from SR 216 to SR 230 occurs, one of three situations can exist. The number of binary 1's contained in the 63 bits being shifted from SR 216 to SR 230 can be zero as detected and indicated by decision logic (DL) 240, greater than zero as detected and indicated by DL 242, or equal to zero as detected and indicated by decision logic (DL) 244. In each of these three DLs, N equals the number of 1's contained in the 63 bits that have been shifted from SR 216 to SR 230. If N is equal to zero, then there is no MSB present. If N is greater than 1, then there must be more than one binary 1 in that group of 63 bits being shifted from SR 216 to SR 230, and DL 242 will provide an output. If N is equal to 1, then there is only one binary 1 in that particular group of 63 bits.

In the case where there are no binary 1's in the group of 63 bits, or more than one binary 1 in the group of 63 bits, then the next 63 bits in SR 230 are shifted back into SR 216, and the next most significant group of 63 bits is shifted from MSR 265 in parallel into SR 216, and the process is repeated.

It is to be noted that this logic process begins with the MSB of all of the 63 products and then works downwardly through the next MSBs, and it is only when there is only one bit position having a binary 1 therein that the largest product of the 63 products stored in register 202 has been determined. In the foregoing event, counter 236 of binary 1's of FIG. 4 will have counted only one binary 1 which will energize DL 240 since N is equal to 1, and N−1=0, indicating that the MB containing the event having the least priority has been determined.

However, it is highly unlikely that the first 63 MSBs compared out of MSR 265 will contain only one MSB. It is much more likely that DL 244 will be energized where N=0. As the next 63 MSBs are transferred from MSR 265 into SR 216 in parallel and then shifted serially into SR 230 where the binary 1's are counted and then shifted back into SR 216, more than one MSB will be found before a single MSB will be found. Therefore, DL 242 will probably be energized, as well as DL 244, several times before DL 240 is energized, which indicates that there is only one MSB in that Nth bit position of the 63 products.

The output of DLs 242 and 244, as well as 240, if FF 280 is set, passes through OR gate 246 to clear input 248 of counter 236 and also to reset to zero counter 250 which counts repeatedly from 1 to 63, representing the number of products or MBs in the system.

It should be noted that, originally, the 63 bits from MSRs 265 are shifted in parallel into shift register 216 and then are shifted serially down to register 230, as mentioned above, by means of output 252 of counter 250 which passes through AND gate 254 and into shift down terminal 256 of serial SR 216. It should also be noted that at the start of operation of the system, a timing pulse D is supplied to lead 258 which sets flip-flop 260, thereby enabling AND gate 254 to permit pulses from counter 250 to pass through AND gate 254 and causing shifting of the 63 bits stored in SR 216 downwardly in a serial manner into SR 230. As these 63 bits are shifted downwardly into SR 230, the bit positions containing a binary 1 are noted by the number 1 binary bit position 262 in SR 230 and are supplied to counter 236 for the ultimate purpose of determining which of the 63 products is the largest product and therefore identifies the MB containing the LPE.

Each time counter 250, which is powered by clock 266, reaches the count of 63, it causes the count-to-2 counter 268 to count from its normal count of two back to a count of one, thereby resetting flip-flop 260 through lead 270. The output of counter 250 will then be supplied through AND gate 272 since flip-flop 260 is reset and will cause the 63 bits to be shifted back upwardly from SR 230 to original SR 216.

It should be noted, however, that the output of any one of DLs 240, 242, or 244 will pass through OR gate 246 to clear counter 236 in preparation for the determination of the number of binary 1's in the next MSB to be transferred to SR 216. Also, the outputs of DLs 242 and 244 are supplied via a second OR gate 276 through a third OR gate 278 to enable the transfer of the next most significant 63 bits of the 63 products from storage register 265 to SR 216 before counter 250 begins shifting the contents of SR 216 down to SR 230. In other words, SR 216 cannot shift the contents thereof which consists of 63 bits from MSR 265 until it receives them from MSR 265.

The time involved for the resetting of counter 250 to zero at the output count of 63 from counter 250 to begin and pass through flip-flop 260 and AND gate 254 to cause a shifting of the contents of SR 216 downwardly into SR 230 is longer than the time period required for the transfer enable pulse transferred through OR gates 276 and 278 to shift the next most significant bits of the 63 products from MSR 265 to SR 216.

Assume now that the second MSBs of the 63 products have been transferred in parallel to SR 216 and the shifting of such bits from SR 216 to SR 230 has begun. As mentioned above, flip-flop 260 has been set by the output of count-to-2 counter 268 so that the output of counter 250 will pass through enabled AND gate 254 to shift such 63-bit word from SR 216 to SR 230. Also, as discussed before, as the 63-bit word passes the first bit period of SR 230, all binary 1's will be counted in binary bit counter 236. Assume that there is only one binary bit in this second group of 63 bits so that DL 240 will be energized and will produce an output which will set flip-flop 280, thereby priming one of the three inputs to AND gate 282 as well as passing through OR gate 246 to clear binary 1's counter 236 and also to reset to zero the 1-to-63 counter 250, thereby allowing counter 250 to recount again through to 63 so that the 63 bits containing the single binary 1 can be transferred from SR 230 back up to SR 216 which will mark the termination of the comparator-computer process to determine the MB containing the LPE.

Since flip-flop 280 is set, the set output thereof is a binary 1. As mentioned above, counter 250 has been reset to zero, and count-to-2 counter 268 now has a count of 2 therein to energize lead 284 so that AND gate 282 is fully enabled through delay 281 and will disable counter 250 from further operation, thus completing the search for the MB containing the LPE, which is the only output lead of SR 216 having a voltage thereon. Assume that such output lead is lead 50 so that MB 50 is, in fact, the MB containing the LPE and is therefore the LPEL.

Decrementing of Event Counters of FIG. 1 and Entering the New Event Into the Proper MBs of FIG. 3

The discussion will now return to a consideration of FIGS. 1-3 to explore how the determination of the memory block having the LPE is used to perform the following tasks.

1. To place (update) the total events of the type of events contained in memory block 50 by 1.

2. To decrement by 1 the total count of the type of event counter of FIG. 1 containing those events of the type found to have the LPE.

3. Entering the total count of the new event received by the system into MB 50 of FIG. 3 in the proper MS, thus replacing the old total amount previously stored therein, replacing the weighting factor (WF) in MB 50 with the WF of the new event, and replacing the new type of event in the proper MS in MB 50, thereby replacing the old type of event.

4. Incrementing the total number of the new type of event in all of those MSs containing a new type of event by 1, with the exception of MB 50, which already has the new event total entered therein.

5. Updating the age of memory block 50 to a zero since the new event has just been entered therein.

6. Updating the age of all of the remaining memory blocks by one minute at predetermined periodic intervals of one minute not related to the entering of a new event.

Referring again to FIG. 3, there are shown two memory banks of the bank of 63 memory blocks (MMB) which the system contains. It is to be understood that the system could contain any desired number of MBs such as, for example, 123 or 247 or 31, according to the capacity of the system desired.

In FIG. 4, lead 50 at the output of SR 216 identifies that MB 50 is associated therewith, and which contains the LPE, and further which is scheduled to be removed upon the occurrence of the next new event. Lead 50 is the input lead of MB 50 below dotted line 350 in FIG. 3 and functions to energize certain inputs of all of the MSs therein, of which there are five, not including address MS 300. These five MSs are identified by reference characters 302, 304, 306, 308, and 310 and are further identified, respectively, by the labels waveform, age, weight factor, total of this type of event, and type of event. Certain additional logic is associated with memory block 50 in FIG. 3, including coincidence logic 312, AND gate 328, rectifiers 324 and 354, and product logic 202. It is apparent that there are also a number of leads entering and leaving memory block 50, which include input, output, decrementing, incrementing, enabling, and clearing leads. It is to be understood that the MSs of MB 50 contain logic which will perform each of these functions but which are considered too detailed and elementary and well within the scope of one of ordinary skill to be included in detail in this specification. They would only unnecessarily complicate an already complex description. It should further be noted that the same LPEL lead number identified by SR 216 of FIG. 4 (such as LPEL 50) also is used to identify the MB which it energizes, such as MB 50 in FIG. 3.

At this time, only the recognition or identification of the old type of event to be decremented in all of the memory blocks containing such type of event will be identified in MB 50, and this occurs in the following manner. Lead 50 from FIG. 4, which is the lowest priority event lead (LPEL), causes the type of event in memory segment 310, which is in binary form, to be supplied via lead cables 314 and 316 to a common three-lead cable 318 which extends to all of the other memory blocks in the system, and, as will be discussed shortly hereinafter, will function to decrement the total of the type of event stored in block 50, which is also located in any other memory block in the system.

The type of event supplied from memory segment 310 is also supplied to rectifier 324 via lead 322 to coincidence logic 312.

Also, by definition, the type of event appearing on three-lead cables 318, 322, and 326 will coincide with the type of event supplied from the type of event MS 310 of MB 50 and will supply an output to one input of AND gate 328 which, by that time, will have been primed by timing pulse F, as is shown in waveform F of the timing chart of FIG. 10. Thus, AND gate 328 is energized and supplies a pulse via lead 330 to the decrement input 332 of MS 308 which contains a total of the type of event in all of the MBs of the MMB which is the same as the type of event stored in MS 310 of MB 50 of FIG. 3. The decrementing of the total of this old type of event occurs because a new event is about to replace the event stored in MB 50 so that the total of such type of event will, in fact, be reduced by 1.

In a similar manner, the type of event contained in memory segment 310 is supplied via cables 318 and 356, rectifier 358, and lead 360 to coincidence circuit 362 of MB 3, for example, which is assumed to contain the same type of event. Thus, coincidence circuit 362 of MB 3 will, along with pulse F, energize or enable AND gate 364 or decrement the total of this type of event contained in MS 369 of MB 3.

It should be noted, however, that in MB 3, the circuit is designed so that output 368 of MS 370 containing the type of event is not energized since LPEL 3 is not energized. As mentioned before, only certain inputs and outputs of the various MSs of any given memory block are energized only when an LPEL is supplied thereto. The necessary additional logic to illustrate this in the drawing of FIG. 3 is not specifically shown since it consists mainly of AND and OR gates, and, if necessary, energizing pulses which can be generated by simple logic in the timing waveform of FIG. 10 by one of ordinary skill in the art. To include all of such minor additional logic would unnecessarily complicate the drawing and the specification beyond that which is believed to be required. This additional logic, which is mentioned above, consists largely of AND gates, OR gates, and additional energizing pulses which can be placed outside the MB or, of desired, the MB can contain some or all of such additional logic.

Returning now to MB 50, below dashed line 350 in FIG. 3, the output of MS 310 containing the type of event of MB 50 is supplied via lead 344 to logic 138 of FIG. 2 and to the decrement input of that particular one of the type of event counters 10 of FIG. 1 which contains the total count of that type of event. Thus, the total count of that type of event contained in that counter of counters 10 (FIG. 1) will be the same as the total of that type of event contained in memory segments 308 and 369 of MBs 50 and 3 of FIG. 3 and, of course, any other MBs in the 63 MBs which contain that particular type of event.

Discussion of FIG. 6

The discussion will now turn to logic 138 of FIG. 2, shown in detail in FIG. 6, for a detailed discussion thereof to examine how the total number of events in any selected MB of FIG. 3 can be employed to decrement the type of event counters within block 10 of FIG. 1, of which there are only seven. Following such explanation of the logic of FIG. 6, the discussion will consider the entry of the new event into the MMB of FIG. 3 from the temporary storage elements of FIG. 1.

Consider now the detailed logic of FIG. 6. In FIG. 3, it can be seen that all of the leads corresponding to lead 344 of MB 50 which go to the logic of FIG. 6 (and FIG. 2) are joined together on a common three-lead cable 376 (FIGS. 6 and 2) and then supplied via another common three-lead cable 380 in FIG. 6. All of the memory segments containing the total types of events are supplied in FIG. 6 via leads 376 and 380 and then to three-lead cable 382 which can be seen to be connected to the seven AND gates 383-389 through common lead 382, with each AND gave having three differently coded input leads. More specifically, most of the seven AND gates 383-389 have one or more inverters, such as inverter 381, in one of the three inputs to its associated AND gate. Only one AND gate, AND gate 389, has no such inverters. The reason for such inverters is to decode the incoming type of event so that it will be recognized by only one of the coded three-lead inputs. The output of only one of AND gates 383-389 will thus be directed to the decrement input of the correct one of the seven up-down counters 390-396 of FIG. 6. It is to be noted that the type of event counters 390, 391, and 392 of FIG. 6 correspond to counters 120, 122, and 124 of FIG. 1 and are one and the same counters.

Assume, for example, that MB 3 of FIG. 3 contains a type 3 event although it could contain any one of the other six types of events. Assume also that MB 50 contains a type 3 event. It will be noted in FIG. 6 that the coding for a type 3 event is a binary 110. However, only MB 50 of FIG. 3 is energized by LPEL 50 from SR 116 of FIG. 4 so that only coding 110 supplied from type of event memory segment 310 of MB 50 of FIG. 3 is energized and will affect the appropriate one of the seven AND gates 383-389 of FIG. 6. An examination of the input of the seven AND gates 383-389 reveals that only AND gate 385 contains the proper inputs 400, 402, and 406 to decode binary input 110 to decrement counter 392 which contains the total number of type 3 events. More specifically, the two binary 1's in the old event coding from MB 50 are supplied to leads 400 and 402 of AND gate 385 of FIG. 6. The zero is supplied to input 404 of AND gate 385 but is inverted to a binary 1 by inverter 406. Therefore, all three inputs to AND gate 385 are binary 1's, and the up-down type of event counter 392 of FIG. 6 will be decremented by 1. No other counter of counters 390-396 will be decremented. However, before leaving FIG. 6, it should be noted that five MBs, 1, 2, 3, 50, and 63, are shown in FIG. 6, whereas only two are shown in FIG. 3. This is largely due to space and drawing convenience. It is to be understood that in both drawings 3 and 6, there are, in fact, 63 MBs represented.

As mentioned before, once the proper one of the seven counters of counters 110 of FIG. 1 is decremented due to the identification of the MB which contains the LPE stored, then the next steps is to enter the characteristics of the newly arrived type of event stored in FIG. 1 into the proper memory segment of the proper MB which, in this case, is MB 50 of FIG. 3.

Entry of New Event Characteristics into the Memory Blocks of FIG. 3

The foregoing is accomplished largely by logic 116 of FIG. 2, which is shown in detail in FIG. 5. The new event, which will be assumed to be a type 1 event, is received from waveform analyzer 100 of FIG. 1 and is supplied via three-lead cable 114 (FIG. 1) to the decoding and gating logic 116 of FIG. 2 which will interpret such three-lead cable carrying code to supply the newly received event to the proper one of the 63 MBs of FIG. 3.

Discussion of FIG. 5

Consider now the detailed logic of FIG. 116 which performs this logical interpretation as shown in FIG. 5. The new type of event is received via three-lead cable 114 which goes to the three switches 413, 414, and 415 of FIG. 5, each of which is controlled to an "on" or "off" position by one-second pulse A supplied in FIG. 1 from waveform analyzer 100 via lead 101.

When the one-second pulse A occurs, FF 412 is set, and switches 413, 414, and 415 become conductive, and the code carried on three-lead cable 114 is passed through three switches 413-415 to either the set inputs of flip-flops 420, 421, and 422 or the reset inputs of flip-flops 420, 421, and 522 through inverter 430, 431, or 432. If all three switches 413-415 are on, then all three flip-flops 420-422 become set, and all three AND gates 436, 437, and 438 become energized upon the occurrence of enabling pulse G shown in the waveform of the timing diagram of FIG. 10. The foregoing occurs only when the type of event is a type 7 event, in which case all of the three inputs to switches 413-415 are binary 1's, as discussed in connection with FIG. 1 in a general sense. If any one of the outputs of switches 413-415 is a zero, then the corresponding flip-flop 420-422 is reset through one of inverters 430-432, and the corresponding AND gate 436-438 is not energized. Thus, the same code that is entered via the three leads 114 of FIG. 5 is supplied through three-lead cable 440 of FIG. 5, which goes to all of the MBs of the MMB of FIG. 3 via three-lead cable 442 of FIG. 5, also shown in FIG. 3, and ultimately to three-lead cable 440 of FIG. 3, also shown in FIG. 5.

It will be seen that three-lead cable 440 is a cable common to all 63 MBs of FIG. 3 and more particularly to all 63 MSs entitled "type of event" which, in MB 3, is MS 370 and in MB 50 is MS 310. The new event can be seen to be entered into such memory block 50 via cable 440 of FIG. 5 and cable 380 of FIG. 3.

The new event will also be entered into coincidence circuits 362 and 312 of MBs 3 and 50 via three-lead cables 446 and 448 and rectifiers 450 and 354. Since the new type of event has already been entered into the type of event memory segment 310 of MB 50 and also into coincident circuit 312 via lead 326, coincident circuit 312 of MB 50 will indicate that the type of event stored in memory segment 310 and the new type of event appearing on leads 440 are the same and will prime AND gate 454 to enable MS 308 of MB 50 to receive the total of the new type 1 event from up-down counter 120 of FIG. 1, as will be discussed below.

Discussion of FIG. 7

Referring now to the logic diagram of FIG. 7, which is a detailed logic diagram of logic block 410 of FIG. 2, there is shown the decoding and gating means by which the count contained in the type of event up-down counter which receives that particular type of event is supplied to the proper memory segment of the proper memory block of FIG. 3.

In FIG. 7, the seven types of events counters corresponding to the seven types of event counters within block 10 of FIG. 1 are identified by reference characters 500-506, respectively, and receive the type of events 1-7, respectively. At the proper time, which occurs as pulse G on lead 554 occurs, the proper one of the seven gating networks 507-513 is connected to that type of event counter which contains the type of event being received. Each of the seven counters 500-506 is connected to one of gating networks 507-513 through one of connecting cables 521-527.

It is to be noted, however, that there is an AND gate between pulse G which is associated with each of gating networks 507-513. These AND gates are designated by reference characters 514-520 and require the energization of both of their two input leads to output a signal which will enable the associated gating network of gating networks 507-513.

One of the inputs to each of the seven AND gates 514-520 is marked G and, as mentioned above, is connected to the common G timing input pulse lead 554. The other inputs to AND gates 514-520 are marked, respectively, C-1, C-2, C-3, C-4, C-5, C-6, and C-7, with the output of one of AND gates 514-520 enabling that gating network of gating networks 507-513 which is associated with the up-down counter containing the type of event being received. The seven inputs C-1-C-7 are received from the output of type of event decoder 110 of FIG. 1 so that only one gating network of gating networks 507-513 will be energized as a new event is being received.

Assume, for example, that an event of type 1 is being received so that input terminal C-1 to AND gate 514 is energized, thus priming AND gate 514. However, AND gate 514 will not enable gating network 507 until the G pulse occurs which happens, as discussed above, only after the MBs containing the old type of event have been decremented by 1 and the counter of counters 10 of FIG. 1 containing the total count of the event to be removed, that is, having the lowest priority, has also been decremented. Reference is made to the timing chart of FIG. 10 to show how the G timing pulse related to the other system timing pulses of FIG. 10.

Once gating network 507 is energized, it will pass the count contained in up-down counter 500 through gating network 507, lead 535, and to the common 16-lead cable 543 which is connected to the input of the total count MSs of each of the 63 MBs. Such total count from up-down counter 500, however, will enter only one of the MBs, that MB being the one selected as containing the LPE. In the example being discussed in this specification, such MB is MB 50, identified by the reference character 561 in FIG. 7. LPEL 50, connected to MB 50, is energized as discussed above in connection with FIG. 4 since MB 50 contains the LPE.

It is to be noted that in the discussion of FIG. 3, MS 308 of MB 50 was enabled to the output of AND gate 454 only when the G pulse was applied to AND gate 454. Thus, upon the energization of MS 308 of FIG. 3 in MB 50, which contains the total of the new type of event and the entry of the total count of the new type of event, including the increment of such total when the new type of event was entered into counter 500 of FIG. 7, such will be entered into MS 308 of MB 50 of FIG. 3.

Also, upon the occurrence of pulse G, the weighting factor will be transferred from weighting factor ROM 146 of FIG. 1 to MS 306 of MB 50 of the MMB of FIG. 3.

Discussion of FIG. 8

The logic shown in FIG. 8 is very similar to the logic of FIG. 7. Accordingly, only a few of the logic elements are shown in FIG. 8, namely, weighting factor ROM 507, gating networks 572 and 574, AND gates 580 and 582, common G timing pulse bus 584, weighting factor memory segments 576 and 578 of MBs 1 and 50, and the LPEL outputs 1 and 50 from the comparator-computer of FIG. 4.

As in FIG. 7, the MB containing the lowest priority event is MB 50 so that input lead 50 of MB 50 is energized and is the only such input that is energized of the 63 LPEL inputs to the 63 MBs. Thus, the weighting factor will be entered into weighting factor memory segment 306 of MB 50 at the same time that the new type of event will be stored in MS 310 of MB 50.

Discussion of FIG. 9

Referring now to FIG. 9, there is shown the logic for updating the ages of the 63 age MSs of the 63 MBs of FIG. 3. As will be recalled, 62 of the 63 MSs will be incremented by one minute, and the remaining age segment will be set to zero.

In the example being discussed, memory block 50, into which the new event is to be entered, is the MB containing age memory segment 304 (FIG. 3), which will be set to zero since the new event is a new event and its age is, in fact, zero at the time it is entered.

In FIG. 9, the timing circuits and pulse forming logic 600 are enabled when an LPEL is selected by the comparator-computer logic of FIG. 4 at the output of shift register 216 of FIG. 4. Nine timing pulses A-I, appearing selectively on output leads A, B, C, D, E, F, G, H, and I, represent the nine timing pulses which are generated in accordance with the timing chart of FIG. 10 (and the descriptions of FIGS. 1 and 1a) to energize various portions of the circuit in the proper time sequence and at the proper time so that the various operations, as discussed above, can occur in such proper time sequence. As discussed above, the age is updated either by one minute or, in case of the age memory segment in the memory block having the LPE therein, will be set to zero when the new event is entered in such memory segment.

In FIG. 9, timing circuits and pulse forming logic 600 supplies eight of the nine timing output pulses (B-I) having a time relationship as shown in the timing diagram of FIG. 10 and each performing a separate function, some of which have already been discussed above. Timing pulse I adds one minute to the age MS of those 62 memory blocks which are not going to receive the entry of a new event. Pulse G is received by the age memory segment in the sixty-third memory block which is going to receive the new event.

For purposes of simplicity, only three memory blocks have been represented, namely, MB 1 having an age indicating section 606 and a logic section 608 with two inputs, one labeled clear and the other labeled +1. The clear input functions, when energized, to clear the age section to zero, and the +1 input functions, when energized, to add one minute to the age of the memory segment.

Second memory block 50 is similar to MB 1 and is the MB which receives the new event. Consequently, its age MS 616 will be set to zero upon the occurrence of pulse G through AND gate 619, both of whose inputs will be energized, one by pulse G and the other by LPEL pulse 50.

It should be noted that all three MBs, 1, 50, and 63, will be incremented by one minute every minute since they all receive the pulse I output from timer 600 of FIG. 9 but only the age MS of MB 50 will be set to zero by this particular new event. It will also be noted that both pulses I and G go to common leads 628 and 630, respectively. The common lead 628 goes directly to +1 input logic 608 of the age MS of MBs 1, 50, and 60 of FIG. 9.

The G pulse output is supplied via lead 632 to common lead 630 which goes to one input of AND gates 617, 618, 619, and 620. The other inputs to AND gate 617-620 are derived from the outputs of shift register 216 of FIG. 4 and correspond to the MBs whose corresponding LPEL outputs are associated therewith. For example, MS 606 of MB 1 is enabled when LPEL 1 from shift register 216 of FIG. 4 is energized, whereas the age MS 616 of MG 50 is enabled when the LPEL of MB 50 from shift register 216 of FIG. 4 is energized. The latter is the example being discussed so that the age MS 616 is energized as well as one of its two inputs, clear and +1. However, only AND gate 619 will be energized so that the clear input to the logic portion of the age MS 616 is energized and the age thereof will be reset to zero. Thus, pulse G from timing circuit 600 will reset the age of age MS 616 of MG 50 to zero, and the setting of the other 62 age memory segments of the other 62 memory blocks will not be affected until the occurrence of the next one-minute incrementing pulse.

Discussion of Flow Chart of FIG. 11

Referring now to FIG. 11, there is shown a flow chart of the logic of the method of the invention. The logic of the flow chart of FIG. 11 represents generally the basic block diagrams of FIGS. 1-4 with a few minor exceptions. In FIG. 11, the equipment is started by suitable means represented by logic block 700 marked "Start." At the start of operation, MMBs 30 of FIG. 3 is completely empty, which will require a different flow of logic when decision logic 716 of FIG. 11 is reached than when MBs 30 are full, as will be described later.

In the flow diagram of FIG. 11, the second logic step 701 labeled "Initializes, Clock and Variables," including the various counters, such as the up-down counters, within block 10 of FIG. 1, the MSs within MMB 30 of FIG. 3 and the timing circuits of FIG. 10, all of which are set to zero (except the clock) by means not specifically shown in FIG. 10.

It is to be understood that when the hardware of FIGS. 1-10 is used rather than a computer program to perform the functions of the hardware of FIGS. 1-10, such hardware will automatically be cleared when turned off, except for clock 650 (FIG. 9), which can either be cleared to zero or continue to run until the next operation of the apparatus represented by the hardware of FIGS. 1-10.

Upon the initialization of the clock and of the variables, the logic flows to decision logic 704 which simply detects the next event occurring in the constantly flowing four-second segment of the ECG waveform obtained from the patient.

More specifically, decision step 704 makes a decision as to whether the recently appearing event contained in logic step 704 is an irregular event. If it is not, then the logic repeatedly flows via leads 712 and 714 back to logic step 704 until another event is detected in the continuously flowing four-second interval of ECG waveform obtained from the patient and examined in DL 704 to determine if it is an irregular event. Assuming that an irregular event is detected in logic 704, then the logic flows to logic step 702 to get and store in preliminary storage devices new event characteristics such as age, weighting factor, type of event, total of such type of event in the entire MMB, and the waveform segment containing such type of event.

The logic then goes to step 716, which determines if all the MBs in the MMB are full. Now, the MMB is, in essence, the block diagram of FIG. 3 and consists of the 63 MBs of MMB 30. In other words, if MMB 30 is full, then each of the 63 MBs contains an event.

If the MMB is not full, then the logic flow goes to logic step 739 to determine the characteristics of such newly acquired event and to store in the MBs of the MMB the type of irregular event that occurred along with its weighting factor, age, and total number of such events received, as discussed in connection with the block diagram of FIG. 1. The logic path then continues to logic step 740 which increments that type of event counter of the counters within block 10 of FIG. 1 corresponding to the new event type received.

Next, the time of occurrence of the newly acquired event is stored in an MS of the proper MB of the MMB of the block diagram of FIG. 3 followed by the calculation of the relative storage age of all of the other events that have been previously stored, as discussed in connection with the logic diagram of FIG. 4, and finally followed by the storage of the sampled ECG waveform as, for example, from temporary storage 54 of the logic of FIG. 1 into the appropriate MS of the MB of MMB 30 of the block diagram of FIG. 3.

Up to this point, that portion of the flow chart of FIG. 11 has been considered which applies to the initial filling-up of the MMB which, in FIG. 3, is represented by the 63 MBs within MMB 30 of FIG. 3.

Assume now, going back to the MMB, full decision block 716, that the MMB is full. The logic then goes to logic 722 to calculate the present priority of all events stored in the MMB which, as indicated above, is now full, that is to say, 63 events are stored in the MMB. Such present priority is determined by multiplying the age (A) of each event by its assigned weighting factor (WF) and then by the number of types (T) of each events stored in all of the MBs of the entire MMB 30 of FIG. 3.

The logic path then goes to logic step 734 to identify the MB storing the LPE. Such MB (herein sometimes called the LPEMB) ultimately replaces the LPE with the newly acquired event. It should be noted that ordinarily the discarding or replacing of the LPE is acquired simply by writing over that LPEMB the contents or characteristics of the newly acquired event.

Next, the logic goes to logic step 730 which decrements the event counter corresponding to the discarded event type. In the block diagram of FIG. 1, such event type counters are contained within block 10 of the block diagram of FIG. 1. It should be noted that the type of event counter corresponding to the event type which is stored in the LPEMB of FIG. 3 causes the decrementing of the corresponding type of event counter within block 10 of FIG. 1, as indicated in logic step 740 of FIG. 11, and which has already been described.

Returning again to the next step in the logic after step 730, the logic leads to logic step 739, which replaces the LPE stored in the LPEMB with the most recently acquired event. Logic steps 739, 740, 746, 749, and 752 have already been discussed and are applicable in that they follow the logic of logic step 739 when the MMB is full, as well as when the MMB is initially being filled to its capacity.

It is to be understood that whether the present invention is implemented by hardware or software, or a combination thereof, it can be implemented in a number of different ways by one of ordinary skill in the art armed with the knowledge of the present specification without the exercise of invention.

For example, the up-down counters of FIG. 1 can be replaced with accumulators which both add and subtract, the main memory bank 30 of FIG. 3 can be replaced by various types of registers, and the multiplier-comparator-selector of FIG. 4 can be replaced by other types of comparators-selectors without departing from the spirit or scope of this invention as defined in the appended claims. Further, the detection of the type of event occurring in the ECG can also be determined by equipment manufactured by Hewlett Packard, Fullerton, Calif.; Marquette Electronics, Inc., Milwaukee, Wis.; SpaceLabs, Inc., Redmond, Wash.; and Nihon Kohden Corporation, Tokyo, Japan.

I claim:

1. A system for storing, on an updated priority basis, segments of an electrocardiogram (ECG) waveform from a patient containing at least one of a plurality of selected abnormal cardiac events, hereinafter referred to as event, said updated priority basis determined by selected characteristics comprising the ECG segment containing a new event not fully processed and stored by said system, type of the new event, age (A) of prior stored, like type events as the new event, weighing factor (WF) of the new event, and total number (T) of like type events stored prior to storing the new event, and comprising:

first memory storage means disposed for temporarily storing the characteristics of each said new event, and for maintaining a current total (T) of each different selected type of said event stored prior to storing the new event, and for incrementing said T of like type, prior stored said events as said new event by one;

second memory storage means comprising N memory blocks (MB's) for storing, where n is a positive integer, and on said updated priority basis upon occurrence of each said new event, the characteristics of N events each stored in a different memory block;

first logic means responsive to said first memory storage means and operative on said second memory storage means for determining a highest product of $(A) \times (WF) \times (T)$ in each said MB, said highest product identifying the memory block of said N memory blocks containing a lowest priority type of said event (LPEMB) and for decrementing by one the value of T contained in each said N memory block containing the like type of event as contained in said LPEMB; and second logic means responsive to the decrementing of T by said first logic means for entering the characteristics of the new event in said LPEMB, replacing the characteristics of a prior stored said event in said LPEMB with the characteristics of the new event, and to increment by one the T in each said MB containing the like type of event as the type of new event now entered into the LPEMB.

2. A system in accordance with claim 1 in which said first logic means comprises:

first comparator logic means responsive to the identification of the LPEMB for comparing the type of event stored therein with the type of event stored in each of remaining N−1 MB's, and, if coincidence exists between said LPEMB and any said remaining N−1 MB's, to decrement the T's of coincident said remaining N−1 MB's by one; and second comparator logic means responsive to the identification of the LPEMB for decrementing by one the T in said first memory storage means of said event type of a like type as in said LPEMB.

3. A system as in claim 1 in which said second logic means comprises:

combination comparator-gating logic means responsive to the completion of the decrementing of the T's in each said MB and in said first memory storage means by said first logic means for entering the characteristics of the new event into said LPEMB, replacing the prior stored event therein; and comparator logic means for comparing the new type of event with the type of event stored in each of the MB's, and, if coincidence exists therebetween in any said MB, to increment the T of that said MB by one.

4. A system as in claim 1 in which said first memory storage means further comprises:

shift register storage means for retaining S seconds, where S is a positive integer, of the ECG waveform from the patient, which ECG waveform is continuously moving through said shift register storage means;

third logic means for identifying and verifying existence of a discrete said event in said waveform continuously moving through said shift register storage means after each said event has been entered into said shift register storage means for V seconds, where V is a positive integer, and where $V \leq S$; and fourth logic means responsive to expiration of said V seconds for storing the event existing in said S second interval of said ECG waveform into said LPEMB after the decrementing of the T's in said MB's and said first memory storage means has been accomplished, and to prepare the system for processing of the next new event in said shift register storage means.

5. A system as in claim 1 and further comprising:

third logic means responsive to said second memory storage means (MB) containing a less than full condition of said events for disabling said first and second logic means and prevent identification of said LPEMB and entering of a said new event into said LPEMB; and fourth logic means responsive to said new event for preparing each successive empty said MB and said first memory storage means for reception of each said new event until all of said MB's in said second memory storage means are filled with said events, said fourth logic means being responsive to the full condition of said second memory storage means to enable said first and second logic means.

6. A system for recording, on an updated priority basis, segments of electrocardiogram (ECG) waveforms each containing at least one of a selected type of irregular cardiac events, hereinafter referred to as event, said event including selected characteristics used to determine said updated priority basis, said characteristics comprising the ECG waveform segment containing the event, the event's type, age (A) of prior stored, like type events as a new event upon occurrence of said new event, the event's weighing factor (WF), and total number (T) of like events as said new event stored prior to a said new event appearing in one of said segments, and comprising:

memory storage means for storing the characteristics of each said new event, and for incrementing said T of prior stored, like type events as said new event by one;

a plurality of N memory blocks (MB's) for storing, where N is a positive integer, on said updated priority basis, said characteristics of each said new event in said segments, each characteristic in a separate MB;

first logic means responsive to said memory storage means and disposed for determining the MB containing a lowest priority event (LPE) by means of an algorithm employing predetermined ones of said characteristics stored in said MB's, said algorithm producing a value in each said MB defining a level of priority of the event in each said MB, and responsive to production of said value in each said MB, identifying the MB containing a lowest priority event as the lowest priority event memory block (LPEMB) and responsive to the identification of the LPEMB, decrementing by one the value of T contained in said LPEMB and the value of T in said memory storage means containing a like type of said events as contained in said LPEMB; and second logic means responsive to the decrementing of T by said first logic means for replacing the characteristics of the event stored in the LPEMB with those of the new event stored in said memory storage means, and for incrementing the value of T in each said MB, other than the LPEMB now containing the new event.

7. A system in accordance with claim 6 in which said second logic means comprises:

first comparator logic means responsive to identification of the LPEMB for comparing the type of event stored in the LPEMB with the type of event stored in each of said MB's and, if coincidence exists between said LPEMB and any said MB, to decrement the T's of coincident said MB's by one; and second comparator logic means responsive to the identification of the LPEMB for comparing the type of event in each said memory bank (MB) of said memory storage means with the type of event in said LPEMB, and if coincidence exists between said LPEMB and any said MB, decrementing by one the T in coincident said memory banks.

8. A system as in claim 7 in which said second logic means further comprises:

combination comparator-gating means responsive to completion of the decrementing of the T's in each said MB and said memory storage means by said first logic means for entering the characteristics of the new event into said LPEMB; and third comparator logic means for comparing the new type of event entered into said LPEMB with the type of event stored in each of other MB's and, if coincidence exists between said new event type in said LPEMB and the event type in any said other MB's, to increment the T's of coincident said other MB's by one.

9. A system as in claim 6 in which said memory storage means further comprises:

shift register means for retaining S seconds, where S is a positive integer, of the ECG waveform from the patient, and which is constantly moving through said shift register means, and;

third logic means for identifying and verifying existence of the new event in said memory storage means after said new event has been in said memory storage means for V seconds, where V is a positive integer and where V<S; and fourth logic means responsive to expiration of said V seconds for entering the new event in said LPEMB after decrementing of the T's in said MB's and in said memory storage means has been accomplished, and to prepare the system for a next said new event.

10. A system as in claim 9 further comprising:

fifth logic means responsive to said N memory blocks containing a less than full condition for disabling said first and second logic means to prevent identification of said LPEMB and entering of a said new event into said LPEMB; and sixth logic means responsive to each said new event in each said segment from the patient, for preparing each successive empty said N MB's in said N memory blocks for receiving said characteristics of each said new event until all said N MB's each contain a discrete said event, said sixth logic means being responsive to a full condition of said N MB's to enable said first and second logic means.

11. A system for recording, on an updated priority basis, segments of electrocardiogram (ECG) waveforms from a patient containing irregular cardiac events, hereinafter referred to as events, said events including certain characteristics used to determine said updated priority basis, said characteristics, for each stored event comprising an ECG waveform segment containing the event, type of the event, age (A) of prior stored, like type events as a new event at occurrence of the new event, the event's weighing factor (WF), and total number (T) of like type of events as said new event stored prior to processing the new event, said system comprising:

memory storage means for temporarily storing the characteristics of each said new event and maintaining a current total (T's) of each different type of said event received, with the current total T of the new event type in said memory storage means being incremented by one;

N memory blocks (MB) for storing, where N is a positive integer, and on said updated priority basis, the characteristics of N said events each stored in a separate said N memory block (MB); and first logic means for multiplying the characteristics $A \times WF \times T$ in each said N memory block (MB) and selecting the MB having a largest product resulting from the multiplication as containing a lowest priority event, herein known as LPEMB, and responsive to said selecting, decrementing the value of T in said MB's and in said memory storage means containing a like type of said event as contained in said LPEMB, and for replacing the characteristics of a recorded said event stored in the LPEMB with those of the new event, and for incrementing the value of T in each said MB, other than the LPEMB, containing said like type of event as the new type of event entered into the LPEMB.

12. A system in accordance with claim 11 in which said first logic means comprises:

first comparator logic means responsive to said selecting of the LPEMB, for comparing the prior stored type of event in the LPEMB with the type of event stored in each of remaining said MB's and, if coincidence exists between the type of event in the LPEMB and the type of event in any said MB, to decrement the T's of the coincident MB's by one; and second comparator logic means responsive to said identification of the LPEMB, for comparing the type event in said LPEMB with the type event in said memory storage means, and if coincidence exists, decrementing by one the T of said MB's means containing a like type of event as contained in said LPEMB.

13. A system as in claim 12 in which said first and second logic means comprises:

gating means responsive to completion of the decrementing of the T's in each said MB and said memory storage means by said first and second logic means, for entering the characteristics of the new type of event into said LPEMB; and third comparator logic means for comparing the new type of event in said LPEMB with the type of event stored in all said N MB's and, if coincidence exists between said new event in said LPEMB and the event in in any said MB, to increment the T of that said MB by one.

14. A system as in claim 11 in which said memory storage means further comprises:
   a temporary storage means for retaining an S second interval, where S is a positive integer, of the ECG waveform from the patient and which is constantly moving through said temporary storage means;
   third logic means for identifying and verifying said new event in said temporary storage means after said new event has been in said temporary storage means for V seconds, where V is a positive integer, and where V<S; and
   fourth logic means responsive to expiration of said V seconds for storing the S second interval containing the new event into said LPEMB after the decrementing of the T's in said MB's and in said memory storage means has been accomplished, and to prepare the system for processing of a next said new event.

15. A system as in claim 11 and further comprising:
   second logic means responsive to less than all of said N memory blocks being filled with said N events, for disabling said first logic means to prevent selection of said LPEMB and entering of a said new event into said LPEMB; and
   third logic means responsive to the new event to prepare each successive empty said N memory blocks for reception of each said new event until all of said N memory blocks are loaded with said events, said third logic means being responsive to a full condition of said N memory blocks to enable said first logic means.

16. A method for recording, on an updated priority basis, segments of an electrocardiogram (ECG) waveform from a patient and containing unusual cardiac events, hereinafter referred to as events, and including certain characteristics used to determine said updated priority basis, said characteristics, for each stored event, comprising the ECG segment containing the event, type of the event, age (A) of prior stored events of a like type as a new event upon occurrence of the new event, weighing factor (WF) of the event, and total number (T) of like said events stored prior to processing and storing of the new event and comprising the steps of:
   temporarily storing in a plurality of storage means the characteristics of each said new event, and including a current total T for each different type of said event received, with the T of prior stored events of a like type as the new event being incremented by one;
   storing, on said updated priority basis initiated by occurrence of each said new event, the characteristics of each said new event in a separate memory block (MB);
   multiplying the characteristics (A)×(WF)×(T) to obtain a product in each said memory block (MB) and selecting the MB containing a largest product as the MB containing a lowest priority event, herein known as the LPEMB, and responsive to the selection of the LPEMB, decrementing by one a value of T in other said MB's and said storage means containing a like type of said event as contained in said LPEMB;
   entering the characteristics of the new event in said LPEMB responsive to the decrementing of the value of T in said MB's and said storage means; and
   replacing the event stored in the LPEMB with the new event and incrementing by one the value of T in each said MB, other than the LPEMB containing a like type of said event as the new event.

17. A method in accordance with claim 16 in which the third step further comprises the steps of:
   comparing the prior stored type of event in the LPEMB with the type of event stored in each of remaining MB's by means of comparator logic and, if coincidence exists between the prior stored event in the LPEMB and the event in other said MB's, decrementing the T's of remaining said MB's by one; and
   comparing the prior stored type of event contained in said LPEMB with coded addresses of each of said plurality of storage means, and if coincidence exists between the event in said LPEMB and the event in any of said plurality of storage means, decrementing the T of that said storage means by one.

18. A method for detecting, recording, and maintaining, on an updated priority basis, segments of a continuously received electrocardiogram ECG waveform from a patient containing selected unusual cardiac events, hereinafter referred to as events, and said updated priority basis determined by characteristics of said events comprising the ECG segment containing a new event, said new event not fully processed and stored by said system, type of the new event, age (A) of prior stored, like type events as said new event at occurrence of the new event, weighing factor (WF) of the new event, and total number (T) of like said events as said new event which occurred prior to storing said new event, and comprising the steps of:
   separately storing in a plurality of first storage means, one discrete first storage means for each different type of said event, the characteristics of each said new event and current totals (T's) for each different type of said events accumulated up to arrival of the new event, with the T of said new event type being incremented by one;
   storing in a separate second storage means comprised of N memory blocks (MB's), where N is a positive integer, and on said updated priority basis with the arrival of each said new event, the characteristics of up to N said events, with the characteristics of each said event stored in a separate memory block (MB);
   multiplying the characteristics (A)×(WF)×(T) stored in each said second storage means responsive to all said N MB's containing a said event and upon occurrence of said new event, to obtain a product for each said MB, said MB containing a highest product selected as the MB containing a lowest priority event (LPE), herein known as the LPEMB;
   decrementing by one responsive to said selection of the LPEMB the T contained in said MB's and in said discrete first storage means containing a like type of said event as contained in said LPEMB; and
   entering the characteristics of the new event in said LPEMB responsive to said decrementing by one in step 4, replacing a prior stored said event therein, and incrementing by one the T in said MB's, other than the LPEMB, which contain the like type of event as the new type of event entered into the LPEMB.

19. A method in accordance with claim 18 in which the fourth and fifth steps further comprise the steps of:

comparing the prior stored type of event in the LPEMB with the type of event stored in each of remaining said MB's by means of comparator logic and, if coincidence exists between the type of event stored in said LPEMB and any said MB, decrementing the T's of remaining said MB's by one; and comparing the prior stored type of event contained in said LPEMB with coded addresses of each said plurality of first storage means to determine which said discrete first storage means contains the T of the type of event stored in said LPEMB and decrementing the T of this said discrete first storage means by one.

20. A method for recording, on an updated priority basis, segments of an electrocardiogram ECG waveform from a patient containing unusual cardiac events, hereinafter referred to as events, and including certain characteristics thereof for determining said updated priority basis, said characteristics comprising the ECG waveform segment containing the event, type of the event, age (A) of prior stored events of a like type as a new event upon occurrence of the new event, weighing factor (WF) of the event, and total number (T) of like events stored upon the occurrence of said new event, and comprising the steps of:

temporarily storing in a plurality of storage means, one discrete storage means for each said type of event, the characteristics of each said new event including individual current totals (T's) for each different type of said event received since arrival of a last said event, with the T of the new event being incremented by one;

storing in a plurality of memory blocks, and on said updated priority basis responsive to occurrence of each said new event, the characteristics of N said events, where N is a positive integer, with the characteristics of each said event stored in a separate said memory block (MB);

determining a lowest priority event (LPE) stored in said plurality of memory blocks by means of an algorithm employing predetermined characteristics of the event contained in each said MB to obtain a value defining a level of priority of that said event and identifying the MB containing the LPE, herein known as LPEMB, and decrementing by one the value of T contained in each said MB, and also in said discrete storage means, of a like type of said event as contained in said LPEMB;

entering the characteristics of the new event in said LPEMB responsive to the decrementing of the T in each said MB and said discrete first storage means; and replacing the prior stored type of said event in the LPEMB with the new type of event and incrementing by one the value of T in each said MB, other than the LPEMB.

* * * * *